(12) United States Patent
Aoki et al.

(10) Patent No.: US 10,542,879 B2
(45) Date of Patent: Jan. 28, 2020

(54) IN-BODY MONITORING CAMERA SYSTEM AND CAMERA UNIT WITH GRIPPING PORTION

(71) Applicant: Sharp Kabushiki Kaisha, Sakai, Osaka (JP)

(72) Inventors: Hitoshi Aoki, Sakai (JP); Kei Urakawa, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 398 days.

(21) Appl. No.: 15/129,044

(22) PCT Filed: Mar. 16, 2015

(86) PCT No.: PCT/JP2015/057744
§ 371 (c)(1),
(2) Date: Sep. 26, 2016

(87) PCT Pub. No.: WO2015/151778
PCT Pub. Date: Aug. 10, 2015

(65) Prior Publication Data
US 2017/0105611 A1    Apr. 20, 2017

(30) Foreign Application Priority Data

Mar. 31, 2014 (JP) ................................ 2014-074024

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00066* (2013.01); *A61B 1/0684* (2013.01); *A61B 1/313* (2013.01)

(58) Field of Classification Search
CPC ....... A61B 1/05; A61B 1/00066; A61B 1/041; A61B 1/053; A61B 1/0676; A61B 1/0684; A61B 1/313
(Continued)

(56) References Cited

U.S. PATENT DOCUMENTS 6,415,823 B1 * 7/2002 Vasek ................. A61M 27/006
138/89
2008/0309758 A1 12/2008 Karasawa et al.
(Continued)

FOREIGN PATENT DOCUMENTS

JP    2010-012222 A    1/2010
JP       4472727 B2    6/2010
(Continued)

OTHER PUBLICATIONS

Official Communication issued in International Patent Application No. PCT/JP2015/057744, dated Jun. 2, 2015.
(Continued)

*Primary Examiner* — Timothy J Neal
*Assistant Examiner* — William B Chou
(74) *Attorney, Agent, or Firm* — Keating & Bennett, LLP

(57) ABSTRACT

It becomes possible to easily retrieve an imaging portion from the inside of a body. When receiving an external force from forceps (33), the gripping portion (22) causes a camera unit (11) to be displaced following displacement of the forceps (33) while maintaining a posture of the camera unit (11) with respect to the forceps (33), and, when receiving an external force other than the external force from the forceps (33), the gripping portion (22) causes the camera unit (11) to rotate with a contact point (61) as a center, or causes the camera unit (11) to rotate so that the contact point (61) is rotationally moved.

7 Claims, 16 Drawing Sheets

(51) Int. Cl.
*A61B 1/06* (2006.01)
*A61B 1/313* (2006.01)
*A61B 1/04* (2006.01)

(58) Field of Classification Search
USPC ........ 600/102, 109, 113, 114, 115, 142, 160, 600/164
See application file for complete search history.

(56) References Cited

U.S. PATENT DOCUMENTS

| | | | |
|---|---|---|---|
| 2009/0018396 A1* | 1/2009 | Takizawa | A61B 1/00147 600/127 |
| 2009/0306470 A1 | 12/2009 | Karasawa et al. | |
| 2011/0046440 A1 | 2/2011 | Asada et al. | |
| 2016/0143510 A1 | 5/2016 | Gotoh et al. | |
| 2016/0234408 A1 | 8/2016 | Urakawa et al. | |
| 2016/0242635 A1 | 8/2016 | Inoue et al. | |
| 2016/0263350 A1 | 9/2016 | Urakawa et al. | |

FOREIGN PATENT DOCUMENTS

| | | |
|---|---|---|
| JP | 4599474 B1 | 12/2010 |
| JP | 2012-239519 A | 12/2012 |
| WO | 2015/020124 A1 | 2/2015 |
| WO | 2015/064743 A1 | 5/2015 |
| WO | 2015/080148 A1 | 6/2015 |
| WO | 2015/080293 A1 | 6/2015 |
| WO | 2015/107848 A1 | 7/2015 |
| WO | 2015/111582 A1 | 7/2015 |

OTHER PUBLICATIONS

Aoki et al., "Camera System for Monitoring Inside of Body", U.S. Appl. No. 15/546,291, filed Jul. 26, 2017.
Gotoh et al., "In-Body Monitoring Camera System and Support Tube for In-Body Monitoring-Camera-System", U.S. Appl. No. 14/899,269, filed Dec. 17, 2015.
Inoue et al., "In-Vivo Monitoring Camera System, and Support Tube for In-vivo Monitoring Camera System", U.S. Appl. No. 15/031,777, filed Apr. 25, 2016.
Urakawa et al., "Intracorporeal-Monitoring Camera System, Support Tube for Intracorporeal-Monitoring Camera System, and Cable Holder for Intracorporeal- Monitoring Camera System", U.S. Appl. No. 14/917,064, filed Mar. 7, 2016.
Urakawa et al., "Camera System for Monitoring Inside of Body, Accessory for Support Tube of Camera System for Monitoring Inside of Body, Fixing Tool for Camera System for Monitoring Inside of Body, and Method for Installing Camera System for Monitoring Inside of Body", U.S. Appl. No. 15/031,816, filed Apr. 25, 2016.
Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.
Aoki et al., "Camera System for Monitoring Inside of Body and Auxiliary Tool Set", U.S. Appl. No. 15/112,726, filed Jul. 20, 2016.

* cited by examiner

IN-BODY MONITORING CAMERA SYSTEM AND CAMERA UNIT WITH GRIPPING PORTION

TECHNICAL FIELD

The present invention relates to an in-body monitoring camera system including an imaging port ion which is introduced into a body.

BACKGROUND ART

Endoscopic surgery is minimally invasive surgery for performing examination or therapeutic treatment without performing a laparotomy for a patient. For the endoscopic surgery, surgical instruments such as forceps and an endoscope are introduced separately into a body cavity of a patient. A surgeon captures an image of a tip part of the surgical instrument, which has been introduced into the body cavity, within an observation field of the endoscope and performs work for the treatment while observing, with the endoscope, a state of a site where the surgical instrument is adapted for treating the patient. For the endoscopic surgery, the surgical instrument and the endoscope are introduced into the body cavity through a pipe that is placed through a body wall (for example, the abdominal wall) in an abdominal part or the like of the patient. Note that, this pipe is a tube-shaped member called a trocar.

The surgeon brings the endoscope close to an organ and enlarges an image of the organ when performing an incision or a suture of the organ, and, at this time, a visual field of the surgeon becomes extremely narrow. Accordingly, demanded is an apparatus with which states in a region outside a working region (for example, motion of surgical instruments outside the working region, a bleeding state, and a residual state of a residue such as gauze) are able to be widely grasped.

PTL 1 discloses that a gripping portion (grasping portion) which is to be gripped with forceps has a freely rotatable structure so that a camera unit is not caught when the camera unit is retrieved through a trocar.

CITATION LIST

Patent Literature

PTL 1: Japanese Unexamined Patent Application Publication No. 2010-12222 (published on Jan. 21, 2010)
PTL 2: Japanese Patent No. 4472727 (issued on Jun. 2, 2010)
PTL 3: Japanese Patent No. 4599474 (issued on Dec. 15, 2010)"
PTL 4: Japanese Unexamined Patent Application Publication No. 2012-239519 (published on Dec. 10, 2012)

SUMMARY OF INVENTION

Technical Problem

PTL 1 discloses an example in which the gripping portion is provided in each of both ends of the camera unit. It is required that one gripping portion is used when the camera unit is attached, and the other gripping portion is used when the camera unit is retrieved.

That is, the gripping portion to be used at the time of attachment is formed by a member which has an excellent rigidity so that the gripping portion is firmly gripped so as to keep a posture of the camera unit. On the other hand, the gripping portion to be used at the time of retrieval is composed of a disk-shaped rotation mechanism or an elastic member (a sponge or the like), and has a configuration by which the posture of the camera unit is easily changed when the camera unit is drawn into the trocar at the time of retrieval. Thus, it is necessary to correctly select the gripping portion to be used at the time of attachment and at the time of retrieval.

Accordingly, with the configuration of the PTL 1, it is necessary to change the gripping portion for grip at a time of insertion and at the time of retrieval by rotating the camera unit or increasing the number of trocars to perform the insertion and the retrieval with different forceps (for example, in directions different from each other). As a result thereof, a problem that the retrieval of the camera unit from the inside of a body is not easy is caused.

The invention is made in view of the aforementioned problem, and an object thereof is to provide an in-body monitoring camera system which allows an imaging portion to be easily retrieved from the inside of a body.

Solution to Problem

In order to solve the aforementioned problem, an in-body monitoring camera system according to one aspect of the invention includes an imaging portion which is introduced into a body, in which the imaging portion includes at least one gripping portion which has an external shape of a circular arc in top view, the at least one gripping portion includes a plurality of grooves, and each of the plurality of grooves extends so as to be a circular arc in top view or a circle in top view and is not formed on an edge of the gripping portion. Moreover, in order to solve the aforementioned problem, an in-body monitoring camera system according to one aspect of the invention includes an imaging portion which is introduced into a body, in which the imaging portion includes at least one gripping portion which has an external shape of a circular arc in top view, and when the gripping portion receives an external force from a medical instrument gripping the gripping portion, the gripping portion causes the imaging portion to be displaced following displacement of the medical instrument while maintaining a posture of the imaging portion with respect to the medical instrument, when the gripping portion receives an external force other than the external force from the medical instrument gripping the gripping portion, the gripping portion causes the imaging portion to rotate with a contact point between the gripping portion and the medical instrument as a center, or causes the imaging portion to rotate so that the contact point is rotationally moved, and the at least one gripping portion includes a groove.

Advantageous Effects of Invention

According to one aspect of the invention, it is possible to easily retrieve an imaging portion from the inside of a body.

BRIEF DESCRIPTION OF DRAWINGS

FIG. 3(c) is a sectional view illustrating a state where the camera support tube and the support tube joining portion which are illustrated in FIG. 1 are joined, FIG. 3(d) is a sectional view illustrating a modified example of the camera support tube and the support tube joining portion, and FIGS. 3(e) and 3(f) are perspective views illustrating modified examples of the camera support tube illustrated in FIG. 3(a).

FIG. 8 is an explanatory diagram regarding an optimum length of a gripping portion, in which FIGS. 8(a) and 8(b) are top views each illustrating the gripping portion having a length within an appropriate range, FIG. 8(c) is a top view illustrating the gripping portion shorter than the appropriate range, and 8(d) is a top view illustrating the gripping portion longer than the appropriate range.

FIG. 9 is a sectional view illustrating a state at a time of retrieving the camera unit illustrated in FIG. 8(a), in which FIG. 9(a) is a view illustrating a state where the forceps are inserted into a trocar, FIG. 9(b) is a view illustrating a state of gripping the camera unit by using the forceps, and FIG. 9(c) is a view illustrating a state where the camera unit passes through the trocar.

FIG. 10 is a sectional view illustrating a case where an external shape of the gripping portion is a substantially rectangular shape in top view, in which FIG. 10(a) is a view illustrating a state of gripping the camera unit by using the forceps, FIG. 10(b) is a view illustrating a state where the forceps are pulled up and the camera unit is pressed against a tip end of the trocar, and FIG. 10(c) is a view illustrating a state where, when the forceps are further pulled up, the camera unit is caught by the tip end of the trocar, and the camera unit is released from the forceps and falls off.

FIG. 11 is a sectional view illustrating a state at a time of retrieving the camera unit illustrated in FIG. 8(b), in which FIG. 11(a) is a view illustrating a state of gripping the camera unit by using the forceps, FIG. 11(b) is a view illustrating a state where the forceps are pulled up and the camera unit is pressed against the tip end of the trocar, and FIG. 11(c) is a view illustrating a state where the forceps are further pulled up to draw the camera unit into the trocar.

FIG. 12 is a sectional view illustrating a state at a time of retrieving the camera unit illustrated in FIG. 8(c), in which FIG. 12(a) is a view illustrating a state of gripping the camera unit by using the forceps, FIG. 12(b) is a view illustrating a state where the forceps are pulled up and the camera unit is pressed against the tip end of the trocar, and FIG. 12(c) is a view illustrating a state where, when the forceps are further pulled up, the camera unit comes into contact with the tip end of the trocar, and the camera unit is released from the forceps and falls off.

FIG. 13 is a sectional view illustrating a state at a time of retrieving the camera unit illustrated in FIG. 8(d), in which FIG. 13(a) is a view illustrating a state of gripping the camera unit by using the forceps, FIG. 13(b) is a view illustrating a state where the forceps are pulled up and the camera unit is pressed against the tip end of the trocar, and FIG. 13(c) is a view illustrating a state where, when the forceps are further pulled up, the camera unit is caught by the tip end of the trocar, and the camera unit is released from the forceps and falls off.

FIG. 14 is a view illustrating comparison between an example in which a sectional shape of the gripping portion is a rectangular shape having a constant thickness and an example of being a tapered shape, in which FIG. 14(a) is a view illustrating a state of gripping the gripping portion with the forceps in the example of the tapered shape, FIG. 14(b) is a view illustrating a state of gripping the gripping portion with the forceps in the example of the rectangular shape, FIG. 14(c) is an enlarged plan view of the camera unit, FIG. 14(d) is an enlarged view of a main part illustrating a state of gripping the gripping portion with the forceps in the example of the tapered shape, and FIG. 14(e) is an enlarged view of a main part illustrating a state of gripping the gripping portion with the forceps in the example of the rectangular shape.

FIG. 15 is a view illustrating examples of groove-shaped patterns of the gripping portions, in which FIG. 15(a) is a view illustrating an example in which a plurality of grooves each of which has an arched shape are formed on the gripping portion, FIG. 15(b) is a view illustrating an example in which a groove is formed along an outer periphery of the gripping portion, FIG. 15(c) is a view illustrating an example in which a circular groove pattern is formed, FIG. 15(d) is a view illustrating an example in which arched grooves are formed and which is a modified example, and FIG. 15(e) is a view illustrating an example in which an elastic material is formed as a non-slip mechanism on a surface of the gripping portion.

DESCRIPTION OF EMBODIMENTS

Embodiments of the invention will be described with reference to FIG. 1 to FIG. 16 as follows. Note that, for convenience of description, the same reference signs are assigned to members having the same functions as those of members indicated in respective embodiments, and description thereof will be omitted appropriately. Moreover, shapes or dimensions (such as a length, a size, or a width) of configurations illustrated in the figures do not exactly represent actual shapes or dimensions, and are appropriately changed for clarification and simplification of figures.

[Configuration of In-body Monitoring Camera System]

Figure 1:
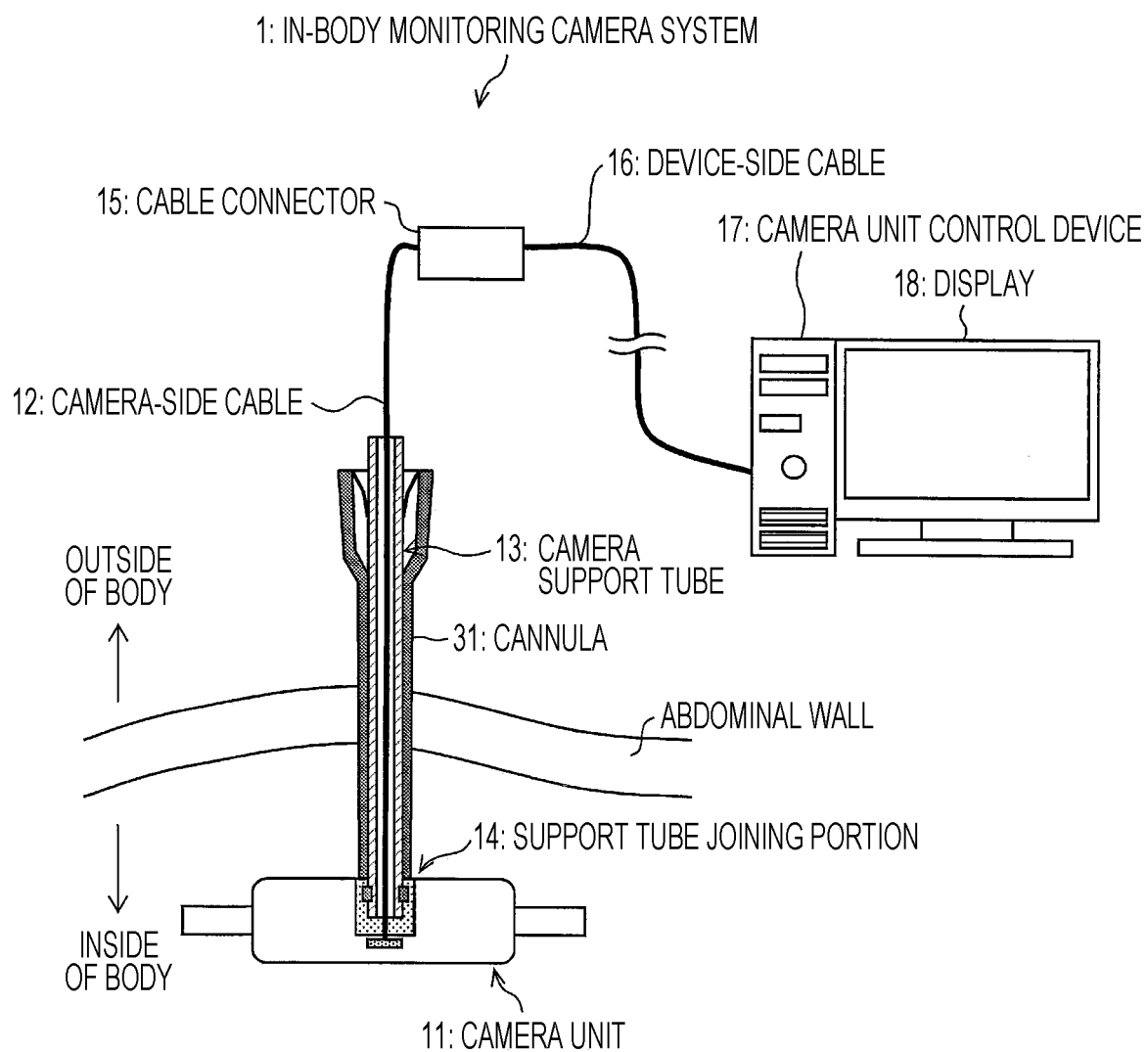
FIG. 1 is a schematic view illustrating a configuration of an in-body monitoring camera system.

FIG. 1 is a schematic view illustrating a configuration of an in-body monitoring camera system.

An in-body monitoring camera system 1 includes an imaging apparatus and a control system. As illustrated in FIG. 1, the imaging apparatus has a camera unit (imaging portion) 11, and a camera-side cable 12 which is connected to the camera unit 11. As illustrated in FIG. 1, the control system has a camera support tube 13, a cable connector 15, a device-side cable 16, a camera unit control device 17 and a display 18.

One end part of the camera support tube 13 is introduced into a body through an inner part of a cannula 31 puncturing an abdominal wall. The camera unit 11 which performs in-body photographing is introduced into the body through a tube-shaped member called a trocar. Then, in a state where the camera-side cable 12 is inserted into an inner part of the camera support tube 13, the one end part (intracorporeal side) of the camera support tube 13 and the camera unit 11 inside the body are joined at a support tube joining portion 14.

The camera unit 11 is connected to the camera unit control device 17 via the camera-side cable 12, the cable connector 15, and the device-side cable 16. Video captured by the camera unit 11 is transmitted to the camera unit control device 17, and a control signal from the camera unit control device 17 is transmitted to the camera unit 11.

The camera unit control device 17 causes the display 18 to display video transmitted from the camera unit 11.

[Configuration of Imaging Apparatus]

Figure 2:
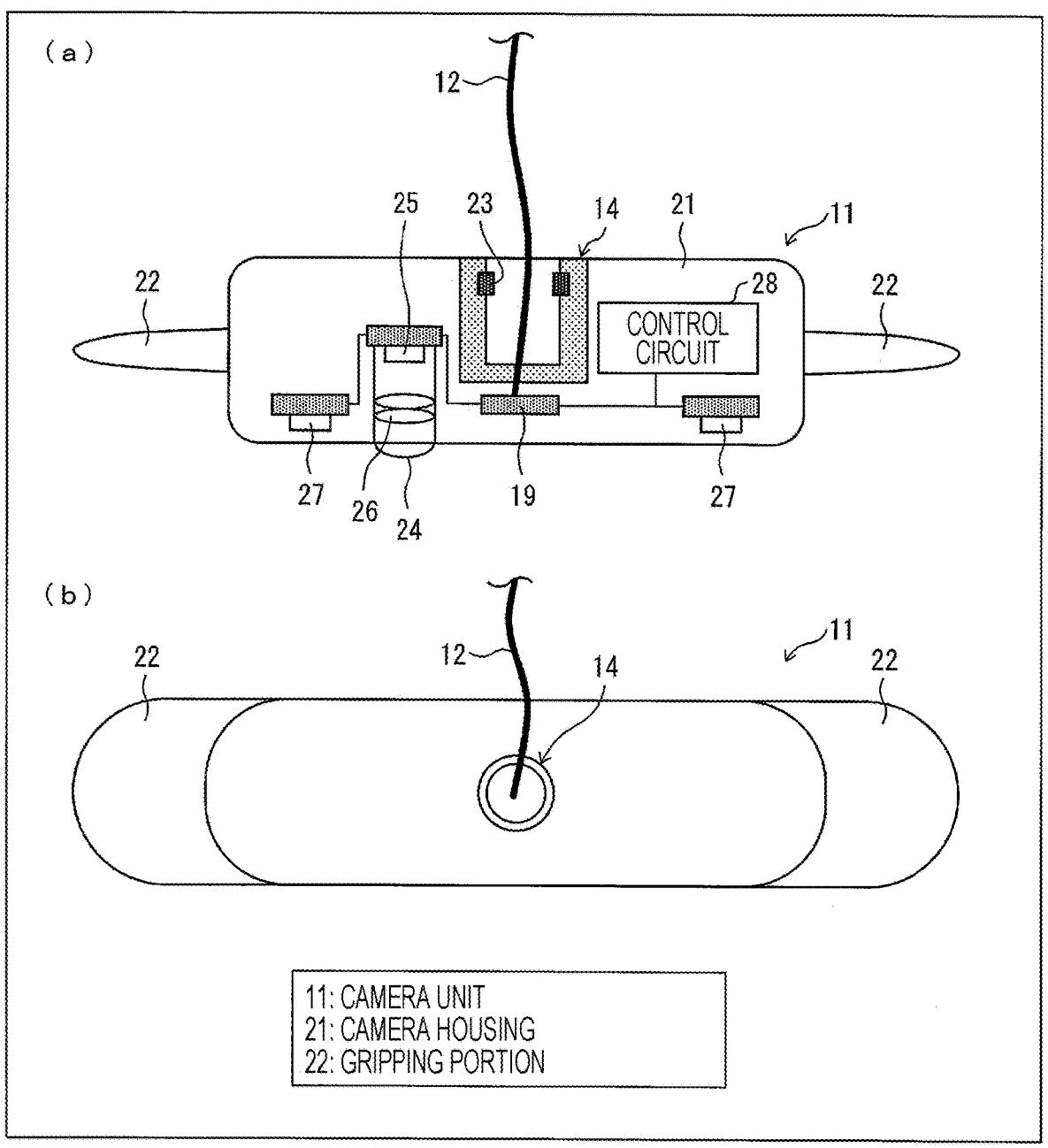
FIG. 2(*a*) is a schematic sectional view of a camera unit according to Embodiment 1, and FIG. 2(*b*) is a top view thereof.

FIG. 2(*a*) is a schematic sectional view of the camera unit according to Embodiment 1 and FIG. 2(*b*) is a top view thereof.

As illustrated in FIGS. 2(*a*) and 2(*b*), the camera unit 11 has a configuration mentioned below.

The camera unit 11 includes a circuit board 19, a camera housing (housing) 21, a solid-state image sensor 25, a lens 26, an illuminating apparatus 27, and a control circuit 28. The circuit board 19, the solid-state image sensor 25, the lens 26, the illuminating apparatus 27, and the control circuit 28 are stored inside the camera housing 21. The solid-state image sensor 25, the illuminating apparatus 27, and the control circuit 28 are electrically connected to the circuit board 19. In a top surface of the camera housing 21, the support tube joining portion 14 having a recessed shape is provided. The support tube joining portion 14 has an aperture structure whose opening is circular and is provided with a locking pawl 23 which has a convex shape, in an inner wall thereof. Further, the camera housing 21 has two gripping portions 22. One of the two gripping portions 22 projects from one of side surfaces of the camera housing 21, which are opposite to each other, and the other one of the two gripping portions 22 projects from the other one of the side surfaces.

The camera-side cable 12 is connected to the circuit board 19 and led out of the camera unit 11 through an inner part of the support tube joining portion 14. The circuit board 19 and a part where the circuit board 19 and the camera-side cable 12 are connected are sealed with resin or the like. Furthermore, in a part (a bottom part of the recess-shaped support tube joining portion 14) of the inside of the support tube joining portion 14, from which the camera-side cable 12 is led out, the camera-side cable 12 adheres and is fixed to the support tube joining portion 14. Examples of the adhesive fixation include sealing fixation with an adhesive agent or an O-ring. Water intrusion, mixing of foreign matter, and the like from the adhesively fixed part into the camera unit 11 are prevented. For being introduced into a body cavity through a trocar, the camera-side cable 12 is formed of a flexible material.

The solid-state image sensor 25 is a CCD (Charge Coupled Device), a CMOS (Complementary Metal Oxide Semiconductor) image sensor, or the like. The solid-state image sensor 25 and the lens 26 constitute an imaging unit 24.

The illuminating apparatus 27 illuminates inside the body to thereby make the video captured by the camera unit 11 clear. It is preferable that the illuminating apparatus 27 has a small size, and an LED (Light Emitting Diode) or the like is used suitably.

Description for Embodiment 1 will be given in detail below.

[Structures of Camera Support Tube and Support Tube Joining Portion]

Figure 3:
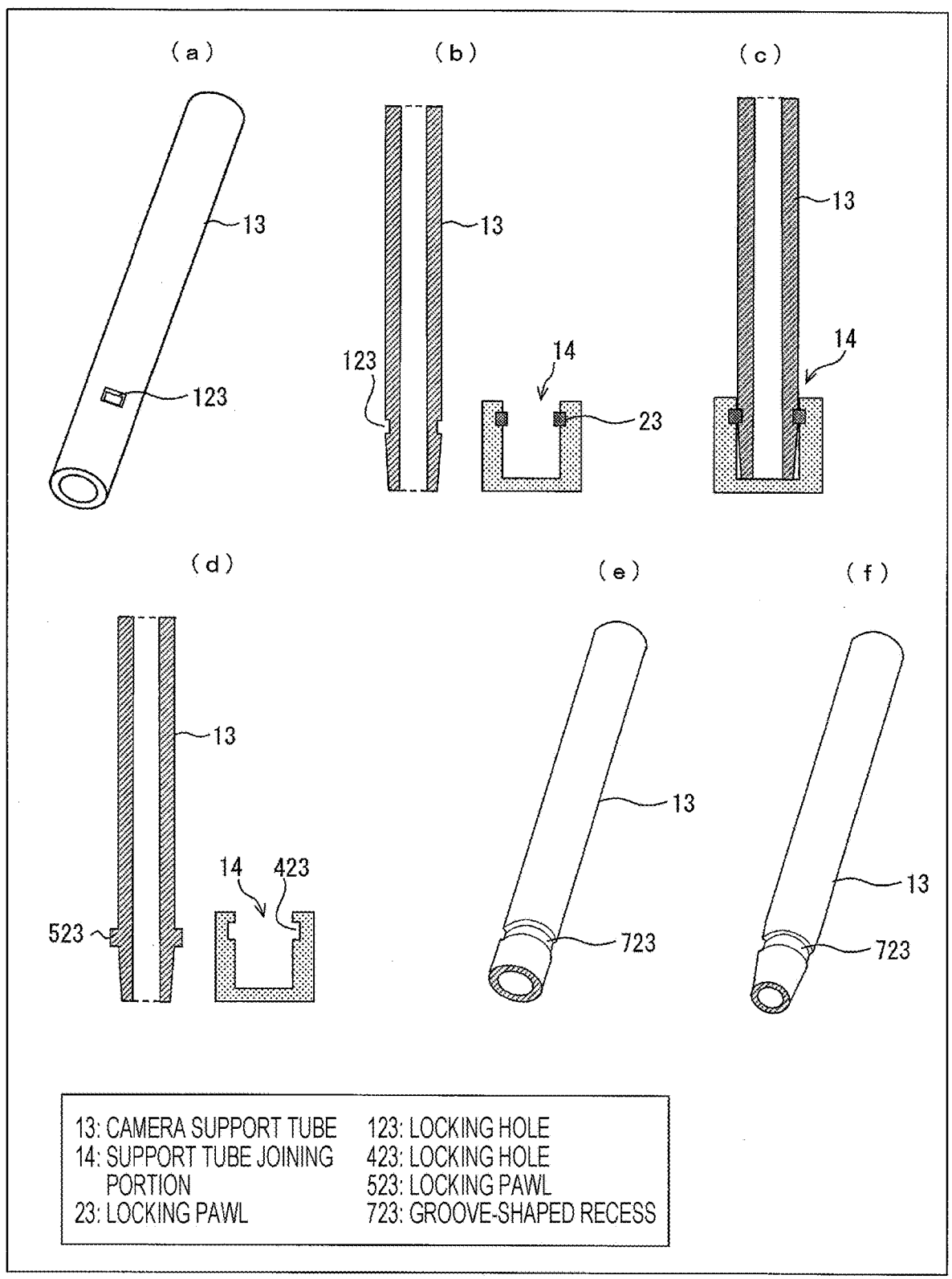
FIG. 3(*a*) is a perspective view of a camera support tube illustrated in FIG. 1, FIG. 3(*b*) is a sectional view of the camera support tube and a support tube joining portion which are illustrated in FIG. 1.

FIG. 3 illustrates schematic structures of the camera support tube and the support tube joining portion.

FIG. 3(*a*) is a perspective view of the camera support tube illustrated in FIG. 1.

As illustrated in FIG. 3(*a*), the camera support tube 13 is a cylindrical tube and has a locking hole 123 which has a recessed shape, in a vicinity of an end part on a side which is introduced into a body. From a viewpoint of joining strength with the camera unit 11, the camera support tube 13 is formed of a hard material.

FIG. 3(*b*) is a sectional view of the camera support tube and the support tube joining portion which are illustrated in FIG. 1, and FIG. 3(*c*) is a sectional view illustrating a state where the camera support tube and the support tube joining portion which are illustrated in FIG. 1 are joined.

When the camera support tube 13 is inserted into the support tube joining portion 14, the locking pawl 23 of the support tube joining portion 14 is to be fit to the locking hole 123 of the camera support tube 13. It is thereby possible to fix the camera support tube 13 to the support tube joining portion 14.

FIG. 3(*d*) is a sectional view illustrating a modified example of the camera support tube and the support tube joining portion, and FIGS. 3(*e*) and 3(*f*) are perspective views illustrating modified examples of the camera support tube illustrated in FIG. 3(*a*).

Instead of providing the locking hole 123 in the camera support tube 13 and the locking pawl 23 in the support tube joining portion 14, as illustrated in FIG. 3(*d*), a locking pawl 523 may be provided in the camera support tube 13 and a locking hole 423 may be provided in the support tube joining portion 14, respectively.

As illustrated in FIG. 3(*e*), a groove-shaped recess 723 instead of the locking hole 23 may be provided in the camera support tube 13. Thereby, it becomes unnecessary to perform an operation of matching positions of the locking hole 123 and the locking pawl 23 when inserting the camera support tube 13 into the support tube joining portion 14, and it becomes easier to join the both, so that the structure is more desirable.

As illustrated in FIG. 3(*f*), the camera support tube 13 may have a structure in which an outer diameter of the tube becomes small from the groove-shaped recess 723 toward the end part on the side which is introduced into a body, that is, may have an external shape of a truncated cone. Specifically, the camera support tube 13 may have a structure in which an inner diameter is set to be fixed and only the outer diameter is changed (the external shape is set to be smaller toward a tip end). Thereby, when an instrument is inserted into the camera support tube 13, it is unlikely to occur the situation, for example, that the instrument is hooked midway (at a narrowed part) and becomes unable to be pulled out, so that the structure is more desirable.

[Insertion of Camera Support Tube into Cannula and Joining Camera Support Tube To Camera Unit]

Figure 4:
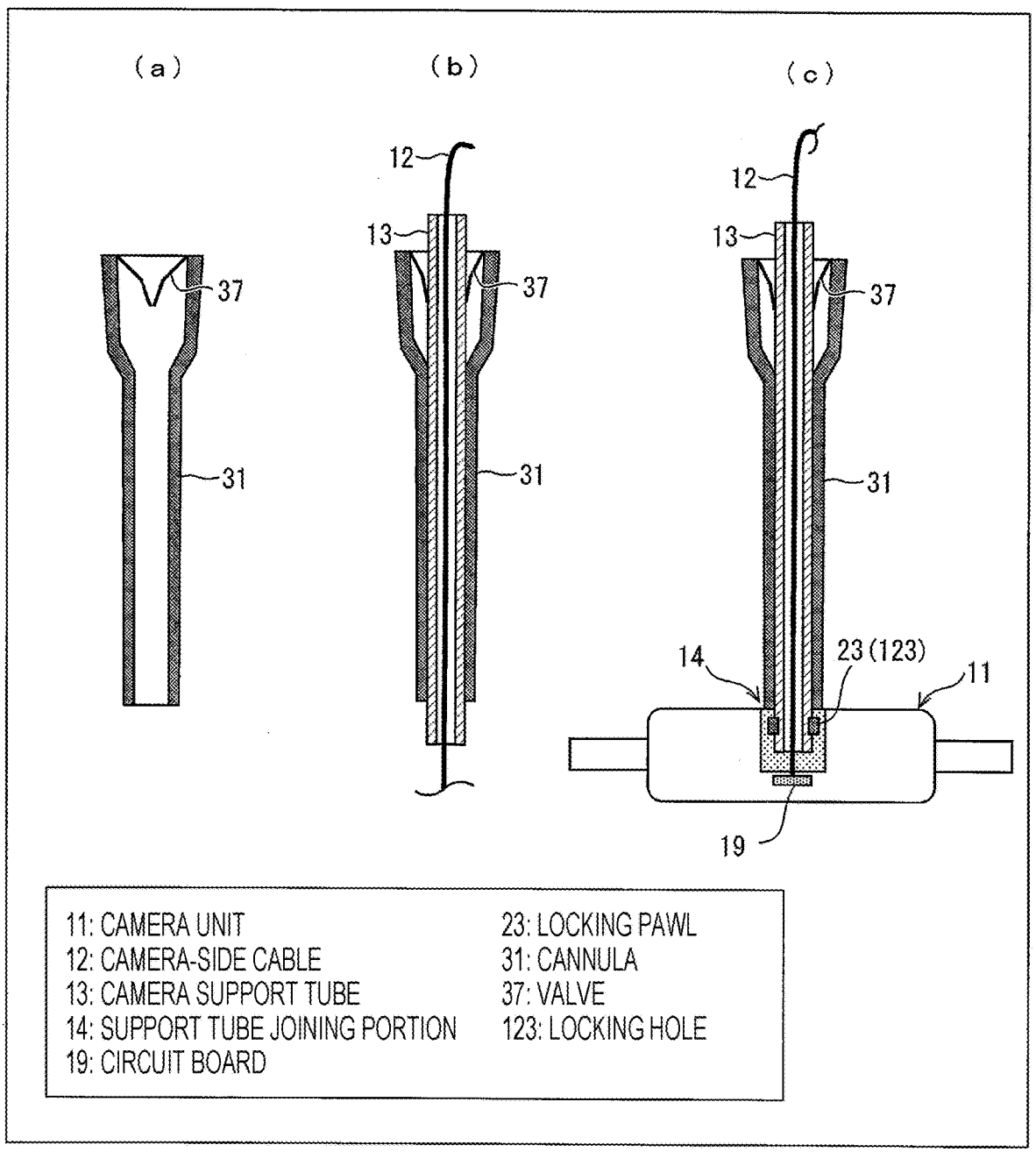
FIG. 4(a) is a sectional view illustrating a structure of a cannula.
FIG. 4(b) is a sectional view illustrating a state where the camera support tube illustrated in FIG. 3 is inserted into the cannula.
FIG. 4(c) is a sectional view illustrating a state where the camera support tube inserted into the cannula and the camera unit which is illustrated in FIG. 2 are joined.
Figure 5:
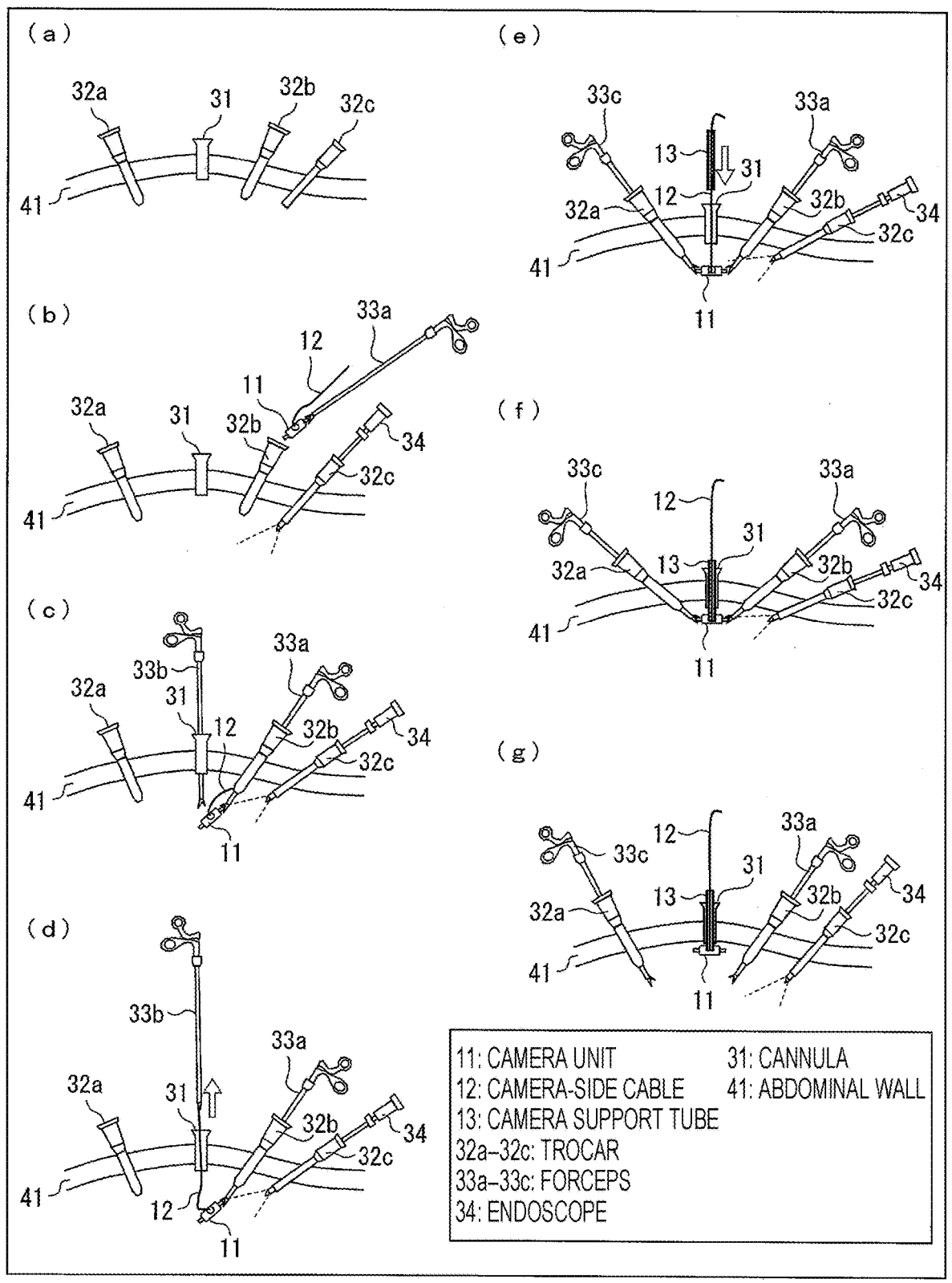
FIGS. 5(a) to 5(g) are schematic views illustrating a method of installing the camera unit in a body.

FIG. 4(*a*) is a sectional view illustrating a structure of the cannula, FIG. 4(*b*) is a sectional view illustrating a state where the camera support tube is inserted into the cannula, and FIG. 4(c) is a sectional view illustrating a state where the camera support tube inserted into the cannula is joined to the camera unit.

As illustrated in FIG. 4(a), the cannula 31 is a tubular device. The cannula 31 has a structure in which one end part thereof (extracorporeal side) is thicker than the other end part (intracorporeal side), and a valve 37 having restorability is provided inside the one end part (extracorporeal side). The valve 37 has, in the middle part thereof, a valve structure which is pressed and expands when external force is applied in a direction from the thicker end part (extracorporeal side) to the thinner end part (intracorporeal side).

In the case of joining the camera unit 11 to the camera support tube 13 inside a body, first, one end part of the camera support tube 13 is pressed against the thicker end part (extracorporeal side) of the cannula 31 in a state where the camera-side cable 12 is inserted into the inner part of the camera support tube 13 as illustrated in FIG. 4(b). The camera support tube 13 is then inserted into the cannula 31 until the one end part of the camera support tube 13 is exposed from the thinner end part (intracorporeal side) of the cannula 31. At this time, the valve 37 is expanded by the camera support tube 13 and tightly fastens the camera support tube 13 with the restorability of the valve 37. As a result thereof, the camera support tube 13 is fixed to the cannula 31. Note that, the other end part (extracorporeal side) of the camera support tube 13 is also caused to be exposed from the cannula 31. Next, as illustrated in FIG. 4(c), by inserting the one end part (intracorporeal side) of the camera support tube 13 into the support tube joining portion 14 by using the camera-side cable 12 as a guide, the locking pawl 23 is fit to the locking hole 123 as described above, and the camera unit 11 and the camera support tube 13 are joined with high mechanical strength.

[Method of Using In-body Monitoring Camera System and Effect Thereof]

FIGS. 5(a) to 5(g) are schematic views illustrating a method of installing the camera unit in a body.

Figure 6:
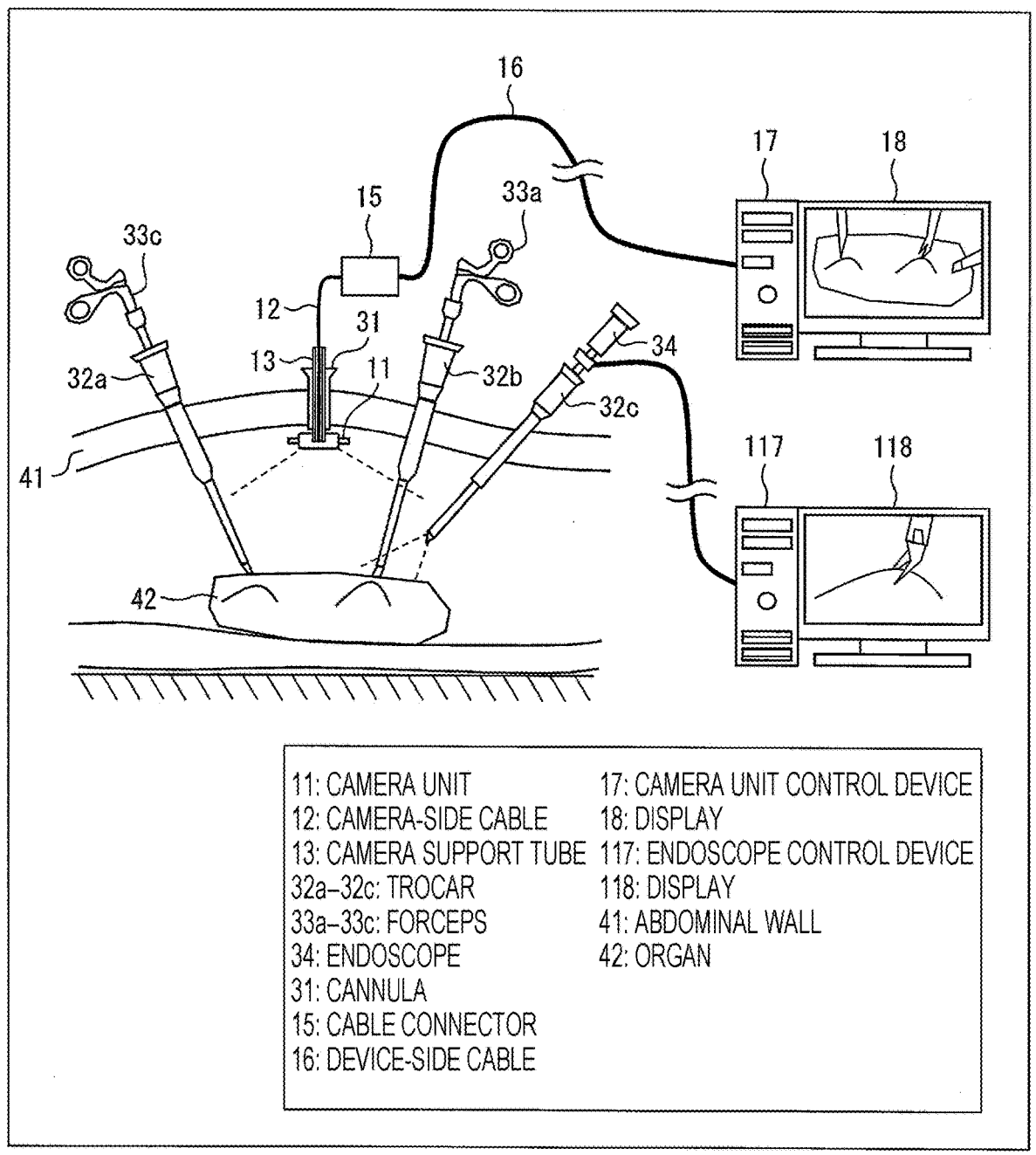
FIG. 6 is a schematic view illustrating a method of using the camera unit.
Figure 7:
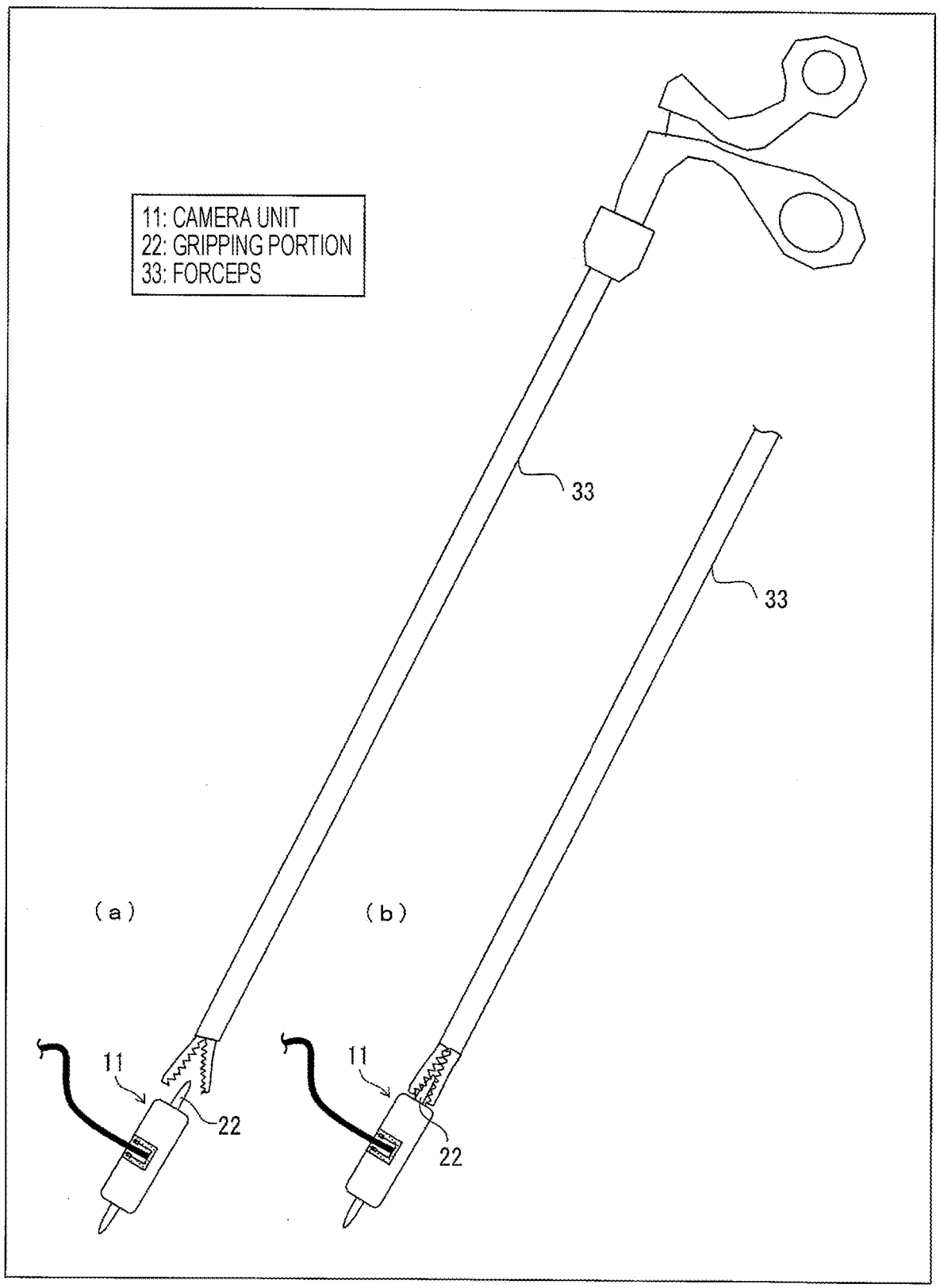
FIG. 7(a) is a view illustrating a state before gripping the camera unit with forceps.
FIG. 7(b) is a view illustrating a state after gripping the camera unit with the forceps.

FIG. 6 is a schematic view illustrating a method of using the camera unit.

As illustrated in FIG. 5(a), first, a surgeon incises a body wall 41 for making a plurality of ports that are holes through which forceps (medical instrument) or an endoscope is inserted into a body cavity, and inserts trocars 32a to 32c into the respective ports. Further, in order to install the camera unit 11 in the body cavity, a port is incised at a position in the body wall 41, from which an entire organ including an affected part is able to be seen, and the cannula 31 is inserted into this port. Specifically, when a needle-shaped obturator punctures the port in a state where the obturator is inserted into the cannula 31, the cannula 31 is inserted into the port.

In order to realize low invasiveness, it is preferable that the cannula 31 has a small diameter. Specifically, it is preferable that the cannula 31 has a diameter of 3 mm or less.

Note that, after at least one of the trocars 32a to 32c is inserted, the surgeon sends gas into the body through the at least one of the trocars 32a to 32c to distend the body cavity in advance. In this manner, a space into which an instrument is inserted is secured.

Next, as illustrated in FIG. 5(b), the surgeon inserts an endoscope 34 into the body cavity through the trocar 32c. Then, the surgeon inserts the camera unit 11 gripped with forceps 33a into the body cavity through the trocar 32b while observing inside the body by using the endoscope 34.

Then, as illustrated in FIG. 5(c), the surgeon operates the forceps 33a to move the camera unit 11 to a vicinity of the cannula 31 and, at this time, inserts forceps 33b into the body cavity through the cannula 31.

Next, as illustrated in FIG. 5(d), the surgeon pulls out the forceps 33b from the cannula 31 in a state where the camera-side cable 12 is held by using the forceps 33b or an exclusive instrument for pulling up, and thereby leads out the camera-side cable 12 to the outside of the body. At this time, the gripping portion 22 of the camera unit 11 is in a state of being gripped by the forceps 33a.

Subsequently, as illustrated in FIG. 5(e), the surgeon inserts forceps 33c into the body cavity through the trocar 32a, and inserts the camera-side cable 12, which has been led out to the outside of the body, into the camera support tube 13 while respectively gripping the two gripping portions 22, which are provided in the both side surfaces of the camera unit 11, by the two forceps 33a and 33c. At this time, the support tube joining portion 14 and an opening of the cannula 31 are to be in parallel and proximate to each other. Thereafter, the camera support tube 13 is inserted into the cannula 31.

Next, as illustrated in FIG. 5(f), by using the camera-side cable 12 as a guide, the surgeon inserts the end part (intracorporeal side) of the camera support tube 13, which is exposed from the cannula 31, into the support tube joining portion 14 and joins the camera support tube 13 and the camera unit 11.

Subsequently, as illustrated in FIG. 5(g), the surgeon pulls up the camera support tube 13 so as to be able to photograph the inside of the body cavity as widely as possible, and causes the camera unit 11 to be in contact with the end part of the cannula 31, which is in the intracorporeal side. Since the camera support tube 13 is tightly fastened by the valve 37 of the cannula 31 (refer to FIG. 4), the camera support tube 13 and the camera unit 11 maintain this posture.

After installing the camera unit 11 in the body, as illustrated in FIG. 6, the camera-side cable 12 and the device-side cable 16 are connected by using the cable connector 15. Thereby, a local video of a treatment part is displayed on a display 118 by an endoscope control device 117, and a video of an entire organ 42, which is captured by the camera unit 11, is displayed on the display 18 by the camera unit control device 17.

Accordingly, while applying treatment by using the forceps 33a and 33c with a working region (local video) being observed in an enlarged view on the display 118, the surgeon is able to grasp states of regions outside the working region on the display 18. Specifically, the surgeon is able to grasp motion of forceps or the like outside the working region, presence/absence of a bleeding place and a bleeding state thereof, a state of a residue such as gauze remaining, and the like.

[Separation between Camera Unit and Camera Support Tube]

Next, a method of separating the camera unit 11 from the camera support tube 13 will be described.

First, the surgeon draws the camera support tube 13 in a direction toward outside the body in a state where the gripping portions 22 of the camera unit 11 in the body are gripped by the forceps 33a and 33c, and pulls out the camera support tube 13 from the support tube joining portion 14 of the camera unit 11.

At this time, similarly to a state illustrated in FIG. 5(f), the surgeon inserts the forceps 33c into the body cavity through the trocar 32a. The surgeon then performs work of detaching the camera support tube 13 by respectively gripping the gripping portions 22 in both the end surfaces of the camera unit 11 with the forceps 33a and 33c so that the support tube joining portion 14 and the opening of the cannula 31 are in parallel and proximate to each other.

Next, the surgeon pulls out the camera support tube 13 from the cannula 31 to separate the camera support tube 13 and the camera-side cable 12, and thereafter leads out the camera unit 11 and the camera-side cable 12 to the outside of the body through the trocar 32a or 32b.

[Summary of Feature Point]

FIG. 7(a) is a view illustrating a state before gripping the camera unit with the forceps, and FIG. 7(b) is a view illustrating a state after gripping the camera unit with the forceps.

In the imaging apparatus of the in-body monitoring camera system 1, as illustrated in FIGS. 7(a) and 7(b), the gripping portion 22 of the camera unit 11 is gripped with the forceps 33 (each of the forceps 33a to 33c). Then, in a state where the gripping portion 22 is gripped, the camera unit 11 is inserted into the body or retrieved from the body through the trocar 32 (each of the trocars 32a to 32c).

As an operation of inserting the camera unit 11 into the body, the forceps 33 is moved linearly with the gripping portion 22 being gripped by the forceps 33 so that the camera unit 11 and the forceps 33 are aligned on a straight line, and then the camera unit 11 is inserted into the trocar 32. Accordingly, the gripping portion 22 is desired to have rigidity so that the forceps 33 is able to firmly grip the gripping portion 22 and a certain posture of the camera unit 11 with respect to the forceps 33 is able to be maintained.

On the other hand, when the camera unit 11 is drawn into the trocar 32 at a time of retrieving the camera unit 11, the camera unit 11 and a gripping part of the forceps 33, which actually performs gripping, are located inside the body. Therefore, an angle at which the forceps 33 grips the gripping portion 22 is restricted depending on a position of the trocar 32 installed. Further, differently from a case of the outside of the body, it is difficult to adjust a positional relationship between the camera unit 11 and the forceps 33 so that the posture of the camera unit 11 and a posture of the forceps 33 represent a straight line. Thus, when the forceps 33 grip the gripping portion 22, the camera unit 11 is greatly inclined with respect to the forceps 33 in many cases. Then, when the camera unit 11 which is greatly inclined with respect to the forceps 33 is drawn into the trocar 32, in the camera unit 11, a great rotating motion is to be generated with a contact point between the gripping portion 22 and the forceps 33 (position at which the forceps 33 grips the gripping portion 22) as a fulcrum. The gripping portion 22 is desired to have an optimum size and include a non-slip mechanism having excellent easiness of rotation so that, when this rotating motion is generated, the forceps 33 does not release the gripping portion 22 or drop the camera unit 11.

A feature of the gripping portion 22 according to each of the embodiments is a mechanism which achieves both the function desired at the time of insertion, and the function desired at the time of retrieval.

That is, the gripping portion 22 according to each of the embodiments has a configuration in which, when receiving an external force from the forceps 33 gripping the gripping portion 22, the camera unit 11 is caused to be displaced following displacement of the forceps 33 while the posture of the camera unit 11 with respect to the forceps 33 is maintained. The gripping portion 22 according to each of the embodiments has, on the other hand, a configuration in which, when receiving an external force other than the external force from the forceps 33 gripping the gripping portion 22, the camera unit 11 is caused to rotate with the contact point between the gripping portion 22 and the forceps 33 as a center, or the camera unit 11 is caused to rotate so that the contact point is rotationally moved.

[Embodiment 1]

The configuration of the gripping portion according to the present embodiment will be described with reference to FIG. 8 to FIG. 13.

Figure 8:
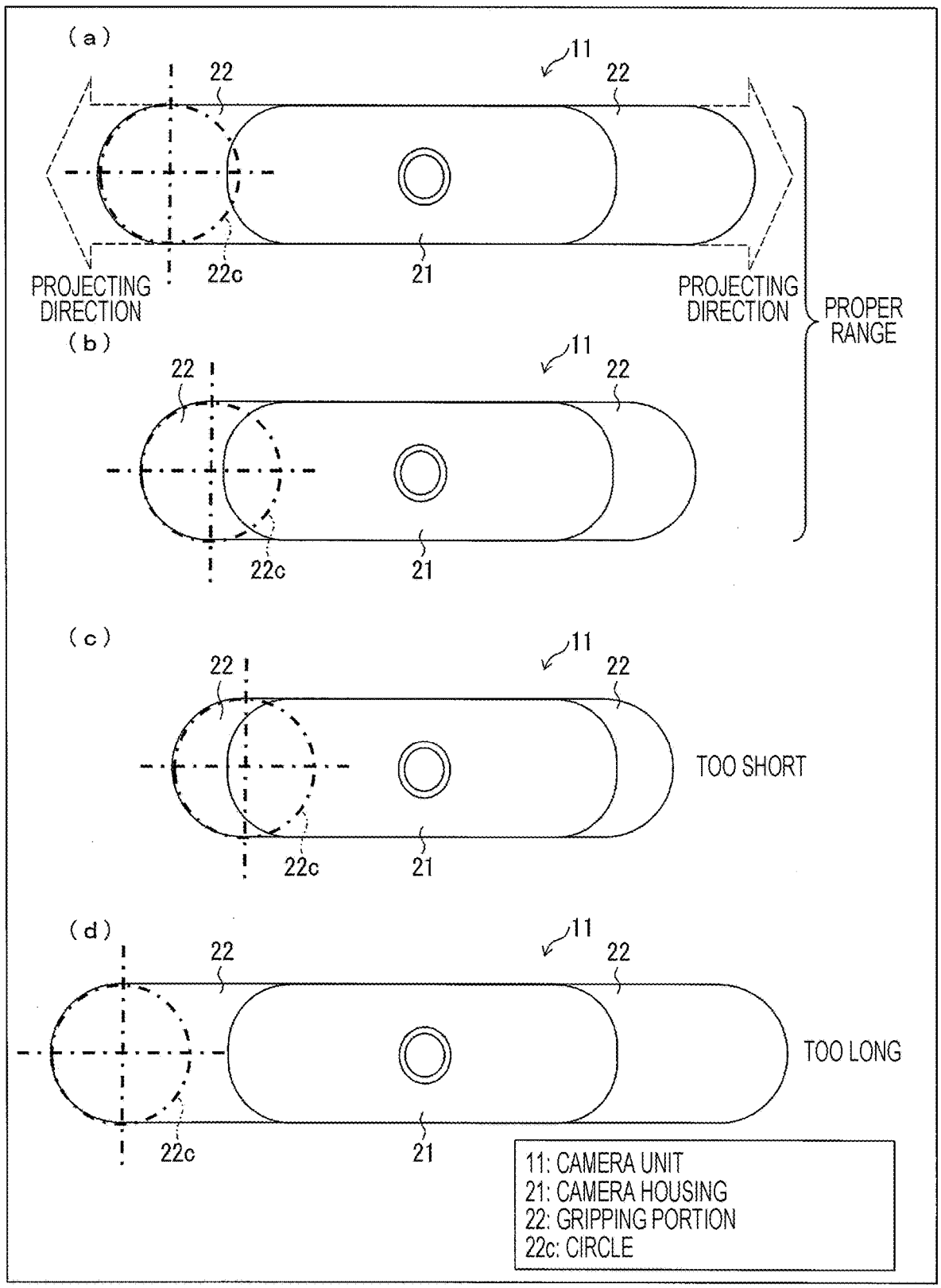

FIG. 8 is an explanatory diagram regarding an optimum length of the gripping portion. FIGS. 8(a) and 8(b) are top views each illustrating the gripping portion having a length within an appropriate range, FIG. 8(c) is a top view illustrating the gripping portion shorter than the appropriate range, and FIG. 8(d) is a top view illustrating the gripping portion longer than the appropriate range.

Each gripping portion 22 illustrated in FIGS. 8(a) to 8(d) projects from the camera housing 21 in a right-and-left direction in the figure (refer to "projecting direction" in FIG. 8(a)), and has an external shape of a circular arc in top view.

Moreover, each gripping portion 22 illustrated in FIGS. 8(a) and 8(b) is an example in which the gripping portion 22 has an appropriate length, and the length of the gripping portion 22 in the projecting direction is equal to or more than a radius and equal to or less than a diameter of a circle 22c which constitutes the external shape (the aforementioned circular arc) of the gripping portion 22. On the other hand, the gripping portion 22 illustrated in FIG. 8(c) is an example in which the length of the gripping portion 22 is too short, and the length of the gripping portion 22 in the projecting direction is less than the radius of the circle 22c. The gripping portion 22 illustrated in FIG. 8(d) is an example in which the length of the gripping portion 22 is too long, and the length of the gripping portion 22 in the projecting direction is more than the diameter of the circle 22c.

Note that, in this case, when the length of the gripping portion 22 in the projecting direction is not constant depending on a place in the gripping portion 22, it is only required that a maximum value of the length (that is, a length of the longest part) of the gripping portion 22 in the projecting direction be equal to or more than the radius and equal to or less than the diameter of the circle 22c.

Hereinafter, regarding functions of the gripping portions 22 having mutually different lengths, a case in which the camera unit 11 is retrieved through the trocar 32 will be described as an example with reference to FIG. 9 to FIG. 13.

Figure 9:
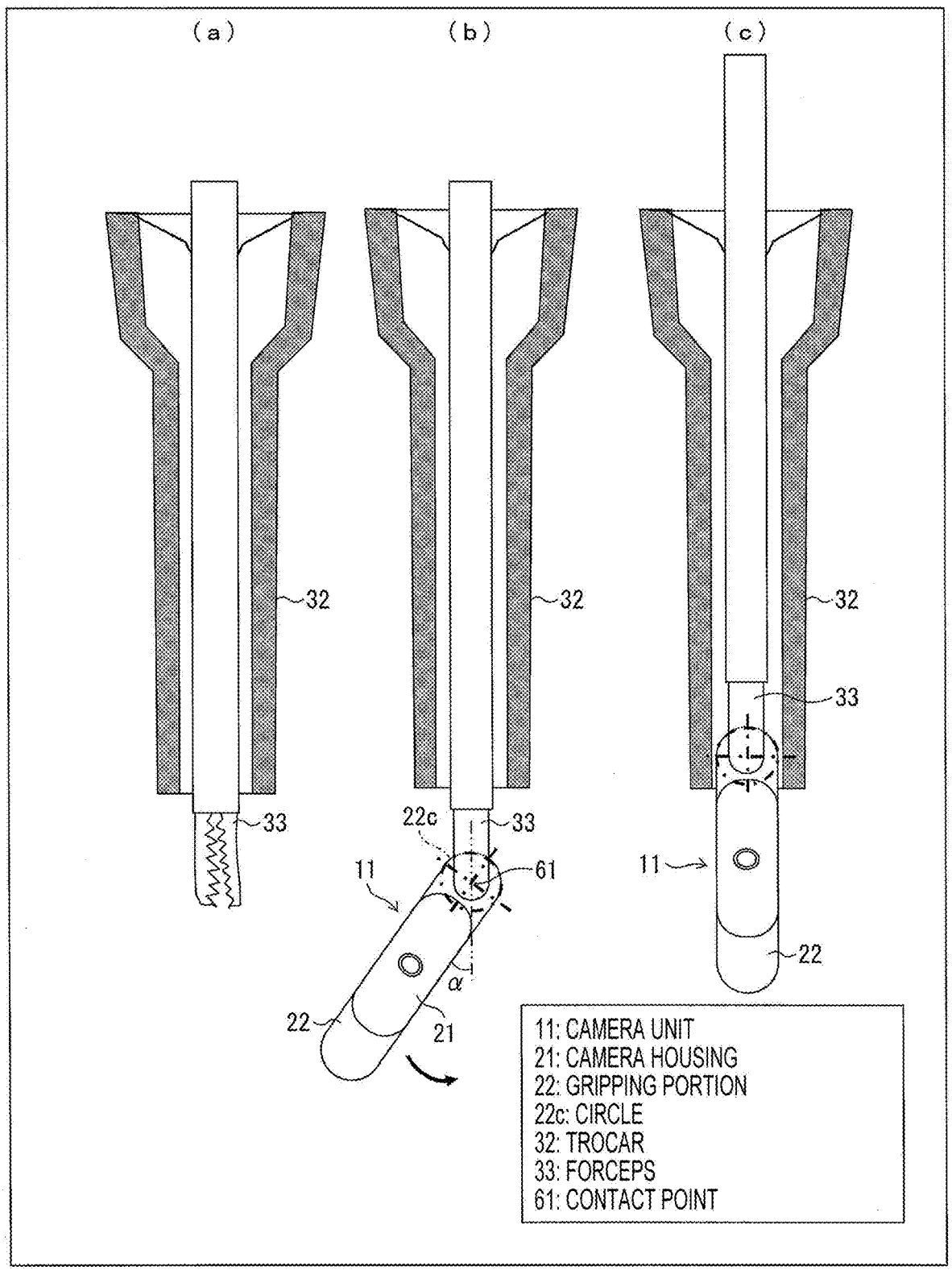

FIG. 9 is a sectional view illustrating a state at a time of retrieving the camera unit illustrated in FIG. 8(a). FIG. 9(a) is a view illustrating a state where the forceps is inserted into the trocar, FIG. 9(b) is a view illustrating a state of gripping the camera unit by using the forceps, and FIG. 9(c) is a view illustrating a state where the camera unit passes through the trocar.

Note that, in order to simplify the illustration, FIG. 9(a) illustrates the sectional view in a state where FIGS. 9(b) and 9(c) are rotated by 90 degrees with an extending direction of the forceps 33 as an axis.

As illustrated in FIG. 9(b), when the gripping portion 22 of the camera unit 11 is gripped with the forceps 33, an angle α formed by the camera unit 11 and the forceps 33 becomes great. As illustrated in FIG. 9(c), when trying to draw the camera unit 11 into the trocar 32 in this state, the gripping portion 22 is pressed against a tip end (intracorporeal side) of the trocar 32, and a rotating motion with a contact point 61 between the gripping portion 22 and the forceps 33 as a center (fulcrum) is to be generated. Since a tip end of the gripping portion 22 has a circular arc shape, and a vicinity of a center of the circle 22c is able to be set as the center of the rotating motion, the gripping portion 22 rotates without great deviation of an edge thereof at a time of the rotating motion. Thus, it is possible to smoothly draw the camera unit 11 into the trocar 32.

It can be said that the case illustrated in FIGS. 9(a) to 9(c) is a case where the fulcrum of the rotating motion is present slightly inside of tip ends of the forceps 33.

Figure 10:
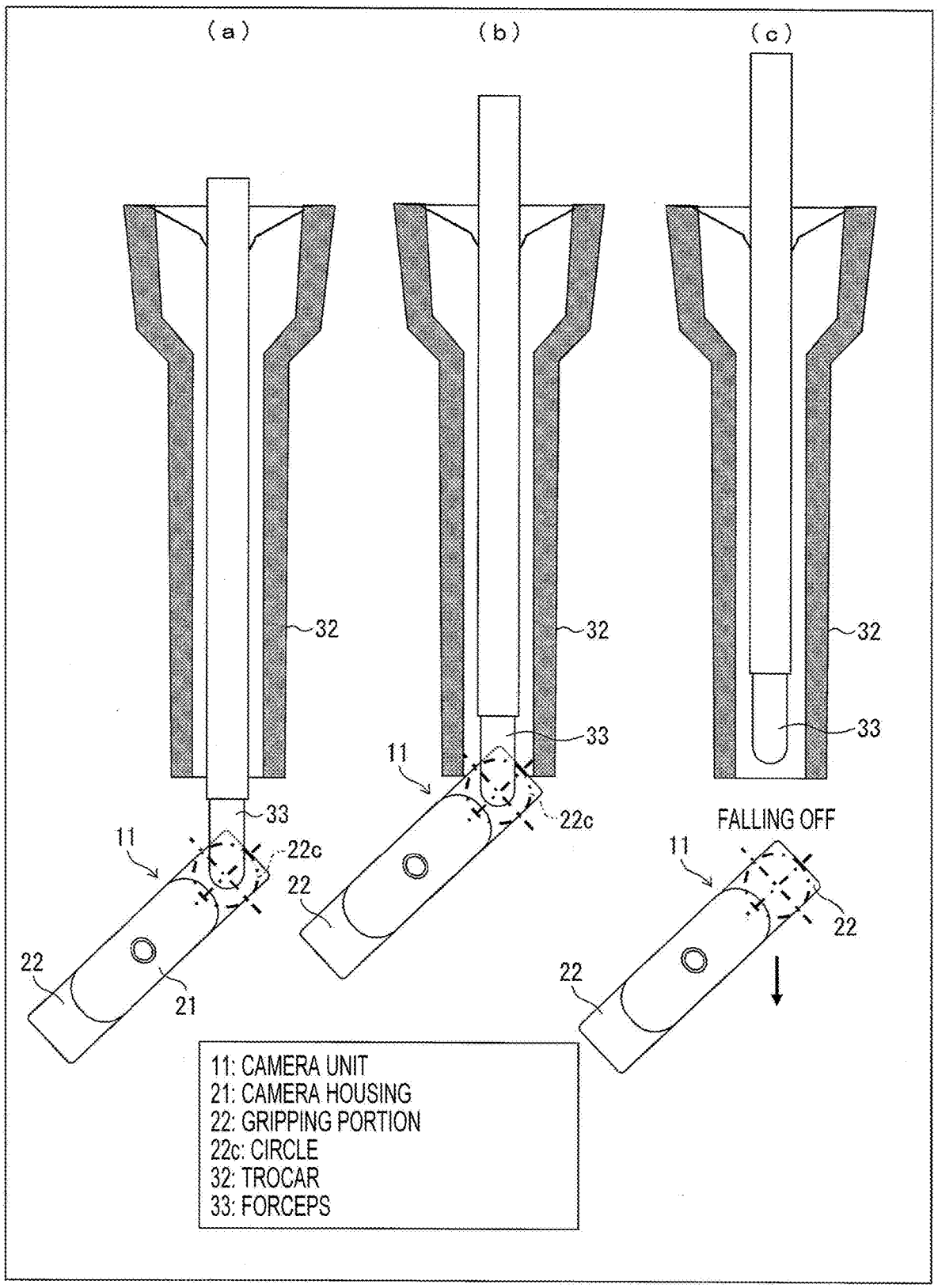

FIG. 10 is a sectional view illustrating a case where the external shape of the gripping portion is a substantially rectangular shape in top view. FIG. 10(a) is a view illustrating a state of gripping the camera unit by using the forceps, FIG. 10(b) is a view illustrating a state where the forceps is pulled up and the camera unit is pressed against the tip end of the trocar, and FIG. 10(c) is a view illustrating a state where, when the forceps is further pulled up, the camera unit is caught by the tip end of the trocar, and the camera unit is released from the forceps and falls off.

As illustrated in FIGS. 10(a) to 10(c), in a case where the external shape of the gripping portion 22 of the camera unit 11 is not a circular arc in top view, there is a disadvantage that a corner of the gripping portion 22 is easily caught by the tip end of the trocar 32, resulting in that the camera unit 11 easily falls off.

In addition, as illustrated in FIGS. 9(a) to 9(c), it is desirable that a width of the gripping portion 22 in a direction perpendicular to the projecting direction is equivalent to a width of the camera housing 21 in the same direction. For example, in a case where the width of the gripping portion 22 is narrower than the width of the camera housing 21, a narrow part is generated on a boundary between the camera housing 21 and the gripping portion 22, and, at a time of pulling up with rotation, the camera unit 11 is easily caught by the tip end (intracorporeal side) of the trocar 32 at the narrow part.

Figure 11:
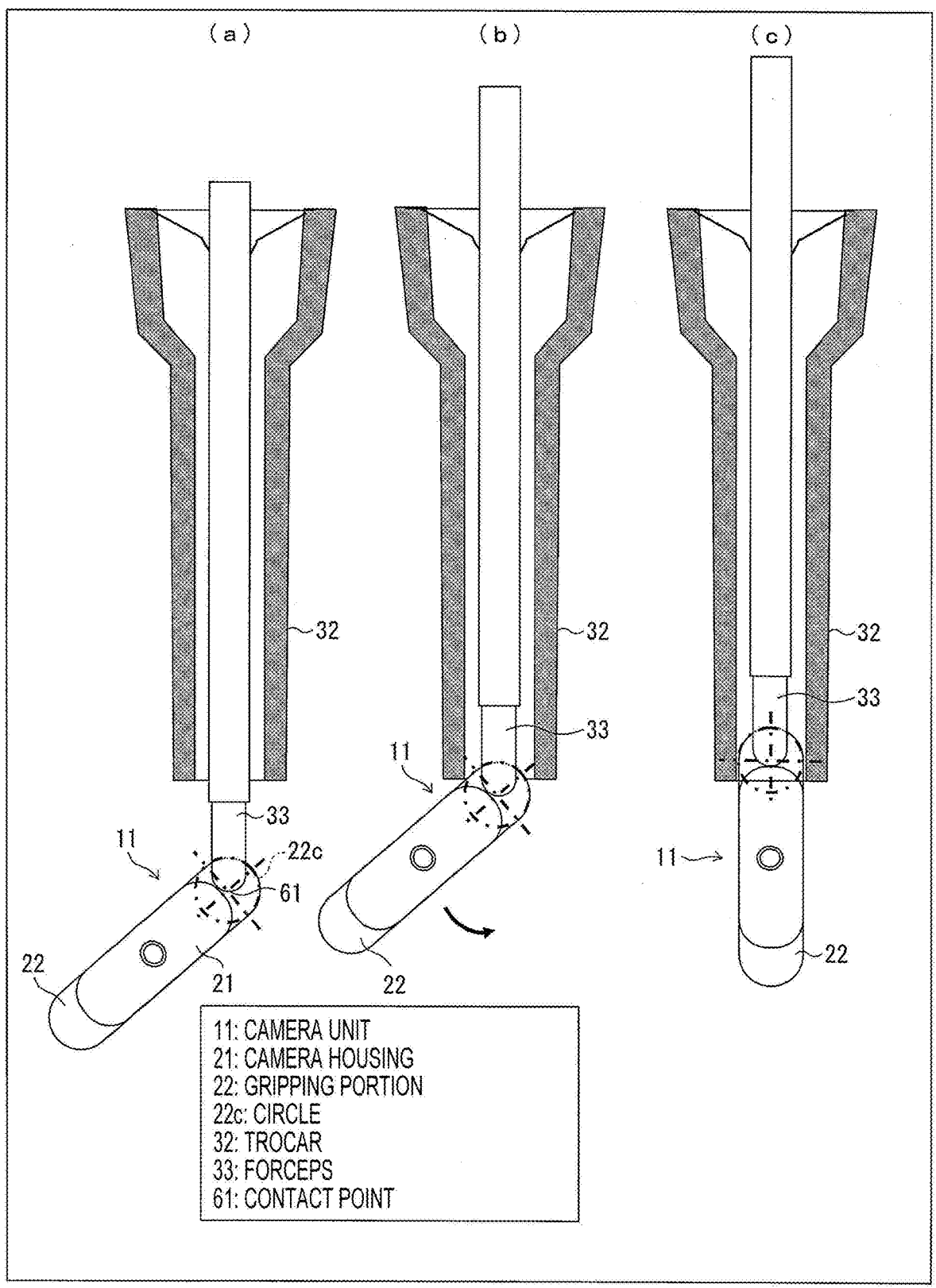

FIG. 11 is a sectional view illustrating a state at a time of retrieving the camera unit illustrated in FIG. 8(b). FIG. 11(a) is a view illustrating a state of gripping the camera unit by using the forceps, FIG. 11(b) is a view illustrating a state where the forceps is pulled up and the camera unit is pressed against the tip end of the trocar, and FIG. 11(c) is a view illustrating a state where the forceps is further pulled up to draw the camera unit into the trocar.

As illustrated in FIG. 11(a), when the gripping portion 22 is gripped with the forceps 33, the forceps 33 and the gripping portion 22 are in contact with each other at the contact point 61. Then, as illustrated in FIG. 11(b), a rotating motion with the contact point 61 as a center is generated. As illustrated in FIG. 11(c), the camera unit 11 is able to be drawn into the trocar 32 without falling off. Depending on a type of the forceps 33, the gripping portion 22 is to be gripped by tip ends of the forceps 33. In this case, according to a case illustrated in FIGS. 11(a) to 11(c), since the vicinity of the center of the circle 22c is able to be set as the center of the rotating motion similarly to the case of FIGS. 9(a) to 9(c), the gripping portion 22 rotates without great deviation of the edge thereof at a time of the rotating motion. Thus, it is possible to smoothly draw the camera unit 11 into the trocar 32.

The gripping portion 22 sufficiently functions as long as the length of the gripping portion 22 in the projecting direction is equal to or more than the radius of the circle 22c.

Figure 12:
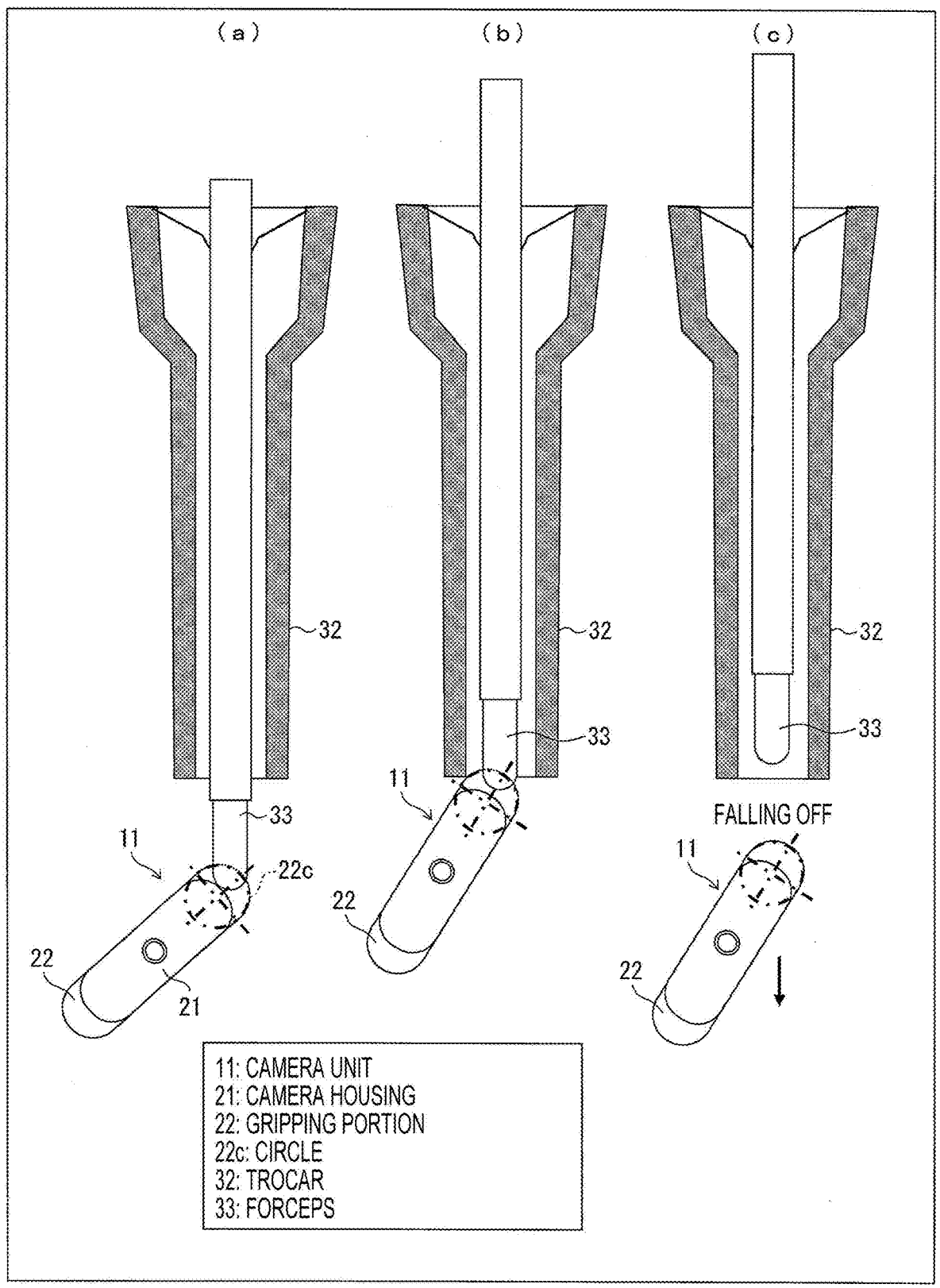

FIG. 12 is a sectional view illustrating a state at a time of retrieving the camera unit illustrated in FIG. 8(c). FIG. 12(a) is a view illustrating a state of gripping the camera unit by using the forceps, FIG. 12(b) is a view illustrating a state where the forceps is pulled up and the camera unit is pressed against the tip end of the trocar, and FIG. 12(c) is a view illustrating a state where, when the forceps is further pulled up, the camera unit comes into contact with the tip end of the trocar, and the camera unit is released from the forceps and falls off.

As illustrated in FIGS. 12(a) and 12(b), since a region which is able to be gripped is small when the gripping portion 22 is gripped with the forceps 33, the gripping portion 22 is to be gripped by using an extremely small part of the forceps 33, and a contact region thereof is small. Accordingly, it is difficult for the forceps 33 to firmly grip the gripping portion 22, and therefore the camera unit 11 is easily released from the forceps 33 due to a small impact caused by a contact with another instrument or the like, as illustrated in FIG. 12(c).

Figure 13:
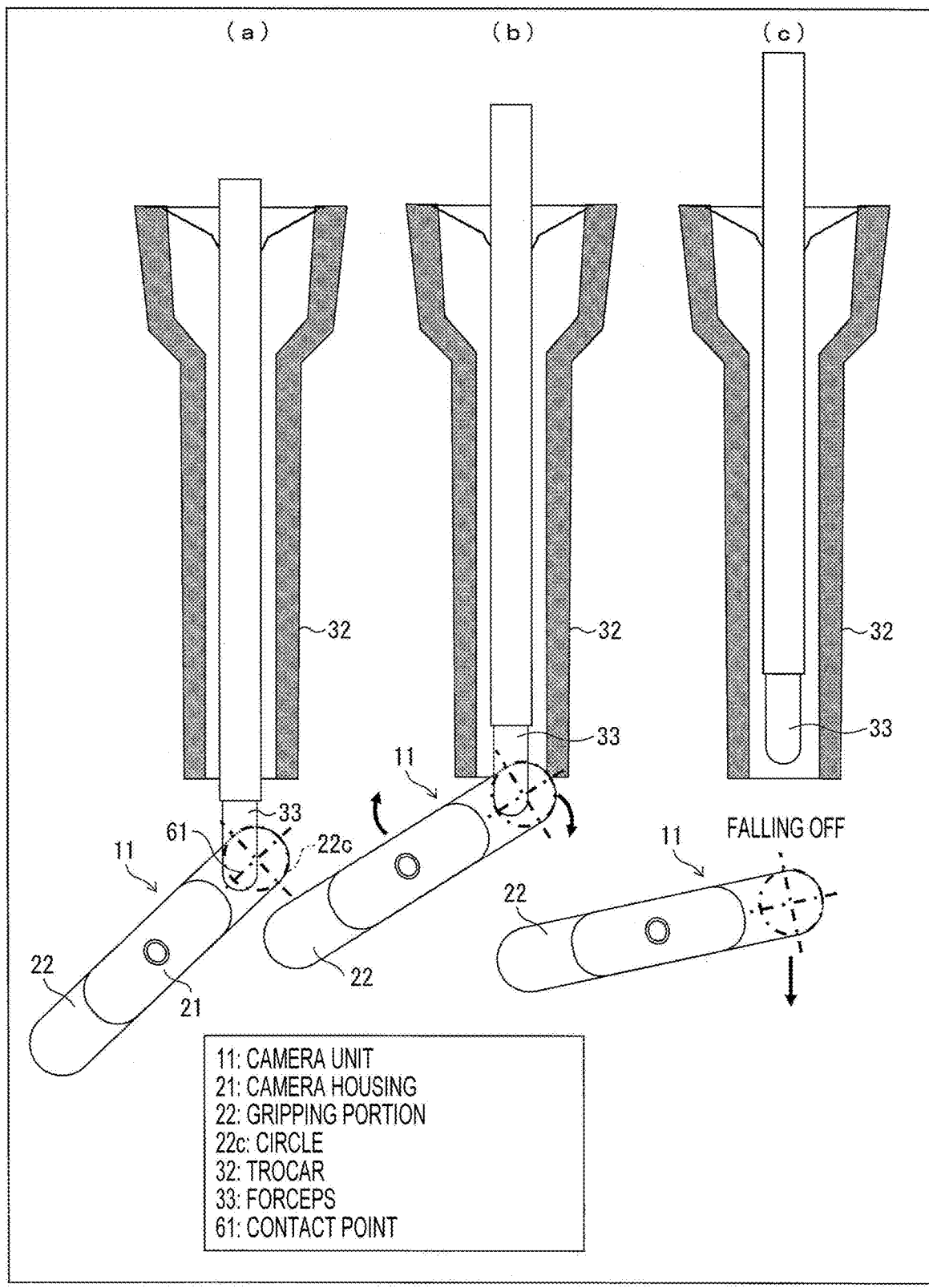

FIG. 13 is a sectional view illustrating a state at a time of retrieving the camera unit illustrated in FIG. 8(d). FIG. 13(a) is a view illustrating a state of gripping the camera unit by using the forceps, FIG. 13(b) is a view illustrating a state where the forceps is pulled up and the camera unit is pressed against the tip end of the trocar, and FIG. 13(c) is a view illustrating a state where, when the forceps is further pulled up, the camera unit is caught by the tip end of the trocar, and the camera unit is released from the forceps and falls off.

As illustrated in FIG. 13(a), in a case where the gripping portion 22 of the camera unit 11 is too long, the forceps 33 grips the gripping portion 22 at the contact point 61 which is greatly apart from the center of the circle 22c in many cases. In this case, as illustrated in FIG. 13(b), when the forceps 33 is pulled up and the camera unit 11 is pressed against the tip end (intracorporeal side) of the trocar 32, a rotating motion is generated in a direction opposite to those of the cases illustrated in FIG. 9 and FIG. 11. Then, the camera unit 11 is easily caught in lateral orientation so as to close the tip end (intracorporeal side) of the trocar 32, resulting in that the camera unit 11 is easily released from the forceps 33 and falls off.

As described above, it is found that it is appropriate that the length of the gripping portion 22 in the projecting direction is equal to or more than the radius and equal to or less than the diameter of the circle 22c.

[Embodiment 2]

Description has been given in detail mainly for the shape of the gripping portion 22 in a schematic plan view (top view) in Embodiment 1. As to a sectional shape of the gripping portion 22 (that is, distribution of thickness of the gripping portion 22), also, there is a structure in which the gripping portion 22 is easily gripped and the camera unit 11 is easily rotated. Hereinafter, a structure (tapered shape structure) in which the gripping portion 22 is formed to be gradually thin toward an edge of the gripping portion 22 will be described.

Figure 14:
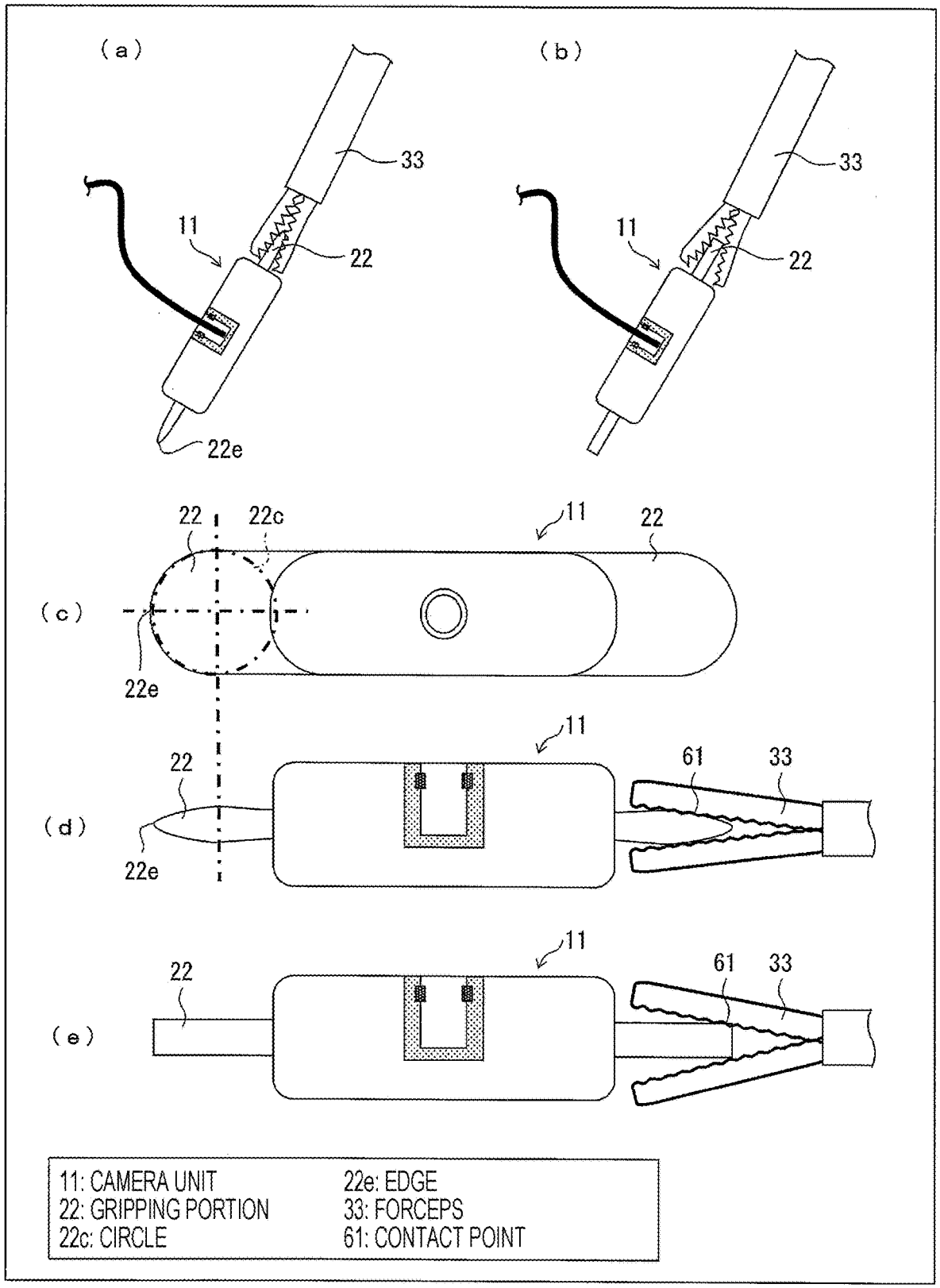

FIG. 14 is a view illustrating comparison between an example in which the sectional shape of the gripping portion is a rectangular shape having a constant thickness and an example in which the sectional shape thereof is a tapered shape. FIG. 14(a) is a view illustrating a state of gripping the gripping portion with the forceps in the example of the tapered shape, FIG. 14(b) is a view illustrating a state of gripping the gripping portion with the forceps in the example of the rectangular shape, FIG. 14(c) is an enlarged plan view of the camera unit, FIG. 14(d) is an enlarged view of a main part in a state of gripping the gripping portion with the forceps in the example of the tapered shape, and FIG. 14(e) is an enlarged view of a main part in a state of gripping the gripping portion with the forceps in the example of the rectangular shape.

Each of the gripping portions 22 illustrated in FIGS. 14(a) and 14(d) has the shape of gradually becoming thin toward an edge 22e of the gripping portion 22. This represents that the sectional shape thereof is the tapered shape.

On the other hand, each of the gripping portions illustrated in FIGS. 14(b) and 14(e) has a uniform thickness throughout the gripping portion 22. This represents that the sectional shape thereof is the rectangular shape.

As illustrated in FIGS. 14(b) and 14(e), in a case where the sectional shape of the gripping portion 22 is the rectangular shape, the contact point 61 between the gripping portion 22 and the forceps 33 is on the edge of the gripping portion 22 and/or in a vicinity thereof. At this time, there is a disadvantage that, when a slip occurs, the forceps easily releases the gripping portion 22. When the gripping portion 22 is formed to be thin, it becomes easy to grip the gripping portion 22 with the forceps 33, but mechanical strength of the gripping portion 22 is to be reduced, and thus it becomes difficult to firmly grip the camera unit 11 with the forceps 33.

Thus, as illustrated in FIGS. 14(a) and 14(d), it is desirable that the gripping portion 22 has the sectional shape of the tapered shape. On the other hand, a structure in which rotation is easily generated near the center of the circle 22c illustrated in FIG. 14(c) is desired. It is desirable to have a structure in which an angle is slightly changed (by about several degrees) (°)) from an angle at which the forceps 33 itself grips the gripping portion 22, and the contact point 61 is positioned at or near the center of the circle 22c.

Moreover, with the structure in which the thickness of the gripping portion 22 is reduced toward the edge 22e, it becomes easy to grip the gripping portion 22 with relatively small forceps, so that any type of forceps may be used for work. Accordingly, workability is improved, and it is possible to reduce time required for installing and retrieving the camera unit 11.

[Embodiment 3]

Though description has been given in detail mainly for the schematic shape (the top view and the sectional shape) of the gripping portion 22 in Embodiments 1 and 2, it is also possible to add a mechanism including the non-slip function to the gripping portion 22 by providing unevenness on a surface of the gripping portion 22, changing a material of the gripping portion 22, or the like. Although an example in which a groove-shaped pattern is formed on the gripping portion 22 will be described below, there is no limitation thereto as long as an equivalent function is included.

Figure 15:
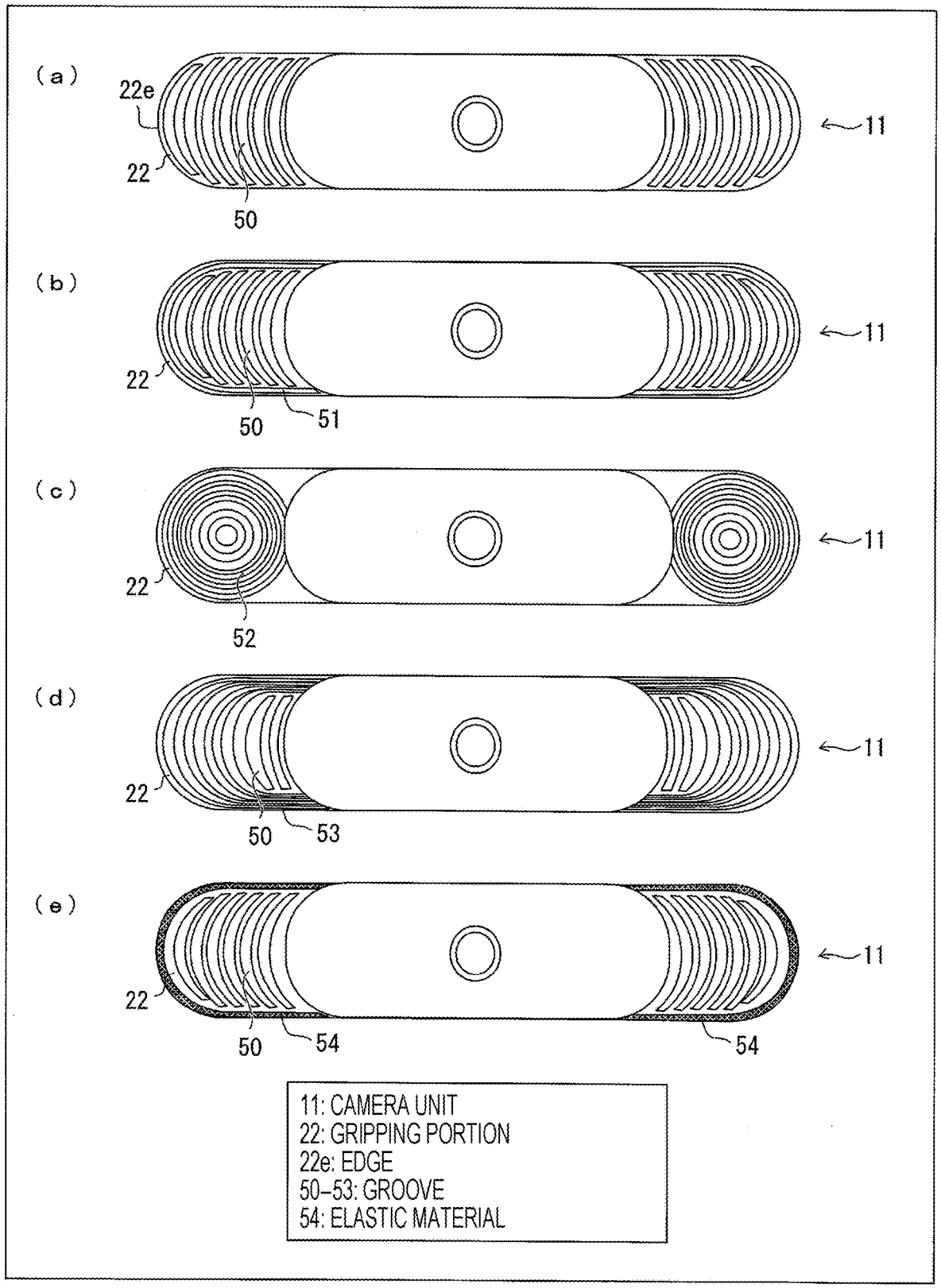

FIG. 15 is a view illustrating examples of groove-shaped patterns of the gripping portions.

FIG. 15(a) is a view illustrating an example in which a plurality of grooves each of which has an arched shape are formed on the gripping portion.

A plurality of grooves 50 are formed on the gripping portion 22 illustrated in FIG. 15(a). Each of the plurality of grooves 50 extends so as to be a circular arc (in other words, an arched shape) in top view. Moreover, none of the plurality of grooves 50 is formed on the edge 22e of the gripping portion 22.

When the gripping portion 22 is gripped with the forceps 33, teeth of the forceps 33 bite into the grooves 50 to firmly grip the gripping portion 22. Thereby, it is possible to reliably transmit a force, with which the forceps 33 pushes or pulls the camera unit 11, to the gripping portion 22, and therefore it becomes easy to displace the camera unit 11 following displacement of the forceps 33.

On the other hand, as described above, when the camera unit 11 is drawn into the trocar 32, the teeth of the forceps 33 slip along the grooves 50 (as if to draw circles) due to a force applied to the camera unit 11 from the trocar 32, and thereby a rotating motion of the camera unit 11 is generated. As a result thereof, similarly to the case illustrated in FIGS. 9(a) to 9(c), for example, the camera unit 11 is able to be smoothly drawn into the trocar 32 without being caught by the trocar 32.

Note that, in a case where the grooves 50 are formed on the edge 22e, the teeth of the forceps 33 slipping along the grooves 50 come off from the edge 22e, and thereby the gripping portion 22 is easily released from the forceps 33. Thus, by providing a configuration in which the grooves 50 are not formed on the edge 22e, it is possible to suppress falling-off of the camera unit 11.

FIG. 15(b) is a view illustrating an example in which a groove is formed along an outer periphery of the gripping portion.

On the gripping portion 22 illustrated in FIG. 15(b), in addition to the grooves 50, a groove 51 is formed along the outer periphery of the gripping portion 22. Even in a case where the teeth of the forceps 33, which slide along the grooves 50, come off from end parts of the grooves 50, the teeth of the forceps 33 remain in the groove 51, and thus it is possible to suppress releasing of the gripping portion 22 from the forceps 33.

FIG. 15(c) is a view illustrating an example in which a circular groove pattern is formed.

A plurality of grooves 52 are formed on the gripping portion 22 illustrated in FIG. 15(c). Each of the plurality of grooves 52 extends so as to be a circle in top view (partially, a circular arc in top view). Moreover, none of the plurality of grooves 52 is formed on the edge 22e of the gripping portion 22.

In this case, spacing between two adjacent grooves 52 in a vicinity of the edge 22e of the gripping portion 22 is less than spacing between two adjacent grooves 52 in the center of the gripping portion 22 and in a vicinity thereof. That is, a pitch between the grooves 52 becomes fine toward an outer periphery side of the gripping portion 22, and becomes coarse toward a center side of the gripping portion 22. This is because, since the forceps 33 is in contact with the grooves 52 mainly near the center of the circle 22c (refer to FIG. 8 and other figures), in a case where the pitch between the grooves 52 in the center side of the gripping portion 22 is too fine, there is a possibility that, when the center of the circle 22c and the contact point 61 (refer to FIG. 9 and other figures) slightly deviate from each other, tooth tips of the forceps 33 bite into the grooves 52 too firmly and a smooth rotating motion of the camera unit 11 is obstructed. When the pitch between the grooves 52 in the center side of the gripping portion 22 is made coarse, appropriate play is generated between the tooth tips of the forceps 33 and the grooves 52, and therefore the camera unit 11 is to be easily rotated. By devising in such a manner, it is possible to provide the structure in which the camera unit 11 is easily rotated. This is similarly applied to the grooves 50 and the groove 51.

Figure 16:
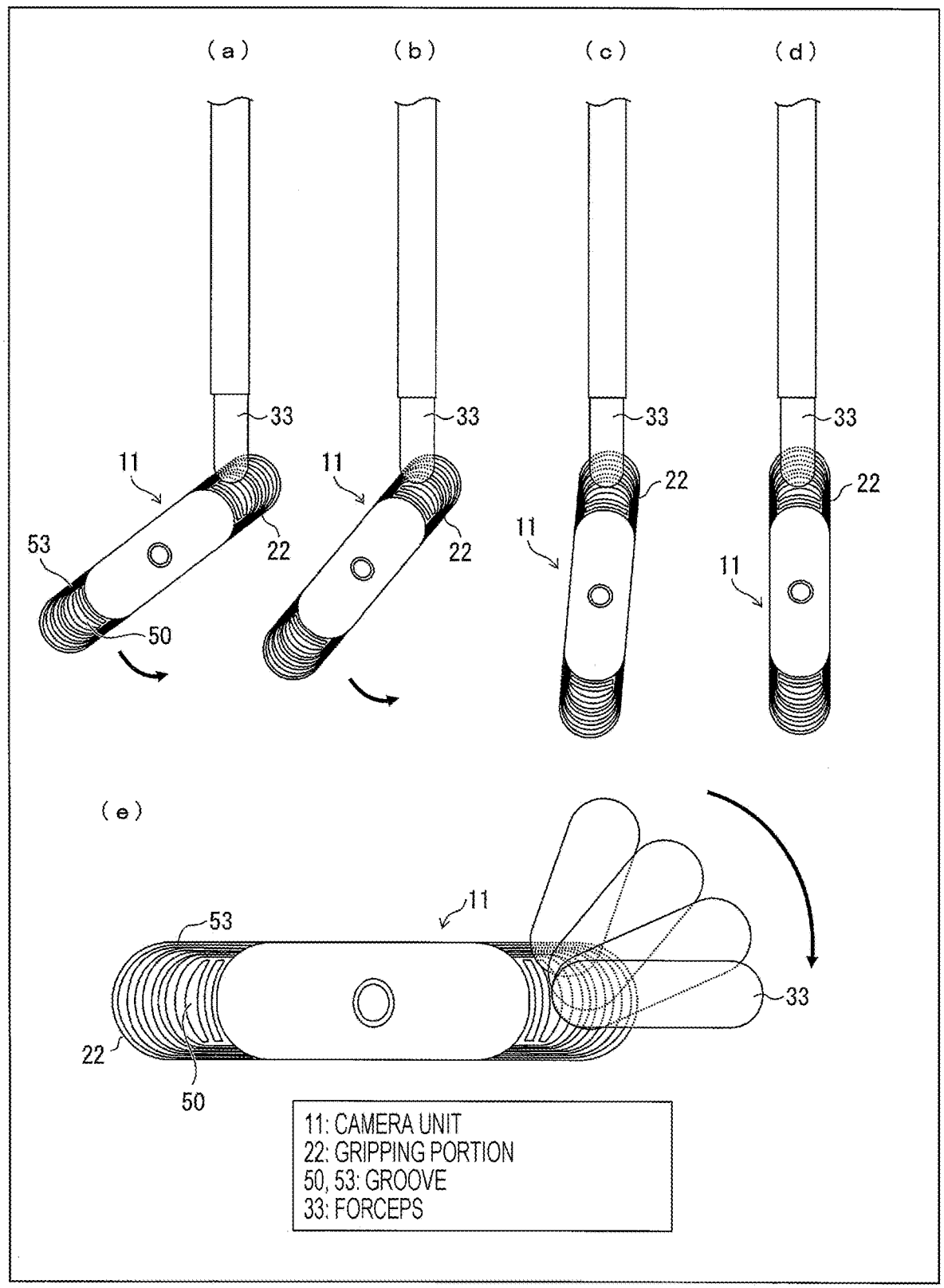
FIGS. 16(a) to 16(d) are views for explaining, with a time lapse, a movement of the camera unit with respect to the forceps when the camera unit illustrated in FIG. 15(d) is gripped with the forceps, a pulling force is applied, and a rotating motion is generated.
FIG. 16(e) is a view for explaining this movement as a movement of the forceps by fixing a camera unit.

FIG. 15(d) is a view illustrating an example in which arched grooves of a modified example are formed. A structure illustrated in FIG. 15(d) will be described by further referring to FIG. 16. FIGS. 16(a) to 16(d) are views for explaining, with a time lapse, a movement of the camera unit with respect to the forceps when the camera unit illustrated in FIG. 15(d) is gripped with the forceps, and then a pulling force is applied, and a rotating motion is generated. FIG. 16(e) is a view for explaining this movement as a movement of the forceps by fixing a camera unit side.

On the gripping portion 22 illustrated in FIG. 15(d), in addition to the grooves 50, a plurality of grooves 53 are formed along the outer periphery of the gripping portion 22. Spacing between two adjacent grooves 53 in the vicinity of the edge 22e of the gripping portion 22 is less than spacing between two adjacent grooves 50 in the center of the gripping portion 22 and in the vicinity thereof.

As illustrated in FIG. 16(a), if the forceps 33 does not capture the vicinity of the center of the circle 22c (refer to FIG. 8 and other figures), and the forceps 33 grips the gripping portion 22 at a position apart from the center, the pulling force is applied between the gripping portion 22 and the forceps 33. This causes a force by which the tooth tips of the forceps 33 slip along the grooves 50 and/or the grooves 53, and the forceps 33 move to an appropriate position (position for gripping in the vicinity of the center). Note that, it is needless to say that, in a case where a direction in which the arched shapes of the grooves 50 and/or the grooves 53 are bent is opposite to a direction for pulling, the tooth tips of the forceps 33 do not move to the center side of the gripping portion 22 but move to a side of the edge 22e, and the forceps 33 may release the gripping portion 22, which is inappropriate. As illustrated in FIG. 16(e), by making pitches of the grooves 53 be fine in the outer periphery side of the gripping portion 22 and coarse in the center side, it is possible to obtain a pattern which achieves both of the movement guide function from an end to a center part and the easiness of rotation which have been described above.

FIG. 15(e) is a view illustrating an example in which an elastic material is formed as the non-slip mechanism on the surface of the gripping portion.

On the gripping portion 22 illustrated in FIG. 15(e), in addition to the grooves 50, an elastic material 54 is formed along the outer periphery of the gripping portion 22. The elastic material 54 is made of, for example, silicone. When the forceps 33 grips the gripping portion 22 at the elastic material 54, the teeth of the forceps 33 bite into the elastic material 54, and a gripping force is markedly improved. However, in this case, as to the center side of the gripping portion 22, since rotation of the camera unit 11 is more facilitated when an elastic material is not provided therein, it is desirable that the elastic material 54 is not provided therein.

As above, description has been given in detail for the configuration in which, as to the surface of the gripping portion 22, the uneven shape is provided, or the material is changed. The same pattern (reversed pattern) of the grooves 50 to 53 and the elastic material 54 may be formed on both surfaces of the gripping portion 22, but, in a case where both the surfaces have the same pattern, a slipping action is caused in the same direction on the both surfaces, so that slip is easily caused. Thus, for a place desired to be less slippery at, for example, the vicinity of the edge 22e of the gripping portion 22, it is desirable that patterns different from each other between the both surfaces of the gripping portion 22 are formed. In addition, even in the center side of the gripping portion 22, it is possible to adopt a method of, for example, combining the configuration of FIG. 15(c) and the configuration of FIG. 15(d) in order to achieve both of the movement guide function and the easiness of rotation. Note that, it is needless to say that there is no limitation to the examples which have been described above.

[Effect: Both of Easiness of Gripping (Strength) and Easiness of Rotation are Achieved]

The gripping portion 22 according to each embodiment has a structure by which, at a time of insertion in a linear direction, a force from the gripping forceps 33 is able to be transmitted to the camera unit 11 as it is, and, at a time of retrieval of the camera unit 11, it is difficult to be released by a rotating motion applied to the camera unit 11. This makes it possible to realize that both of the gripping strength and the easiness of rotation are achieved, installing work is speeded up, and the camera unit 11 is prevented from being contaminated due to falling off. Accordingly, it is possible to reduce time required for the installing work of the camera unit 11, and prevent time of surgery from being increased due to the installation. Moreover, the installing work becomes easy, and thus does not cause stress to a surgeon, so that a degree of safety is increased also from a viewpoint of a human mental effect.

[Overview]

An in-body monitoring camera system according to an aspect 1 of the invention includes an imaging portion (camera unit 11) which is introduced into a body, in which the imaging portion includes at least one gripping portion which has an external shape of a circular arc in top view, and when the gripping portion receives an external force from a medical instrument (forceps 33) gripping the gripping portion, the gripping portion causes the imaging portion to be displaced following displacement of the medical instrument while maintaining a posture of the imaging portion with respect to the medical instrument, and when the gripping portion receives an external force other than the external force from the medical instrument gripping the gripping portion (for example, the trocar 32), the gripping portion causes the imaging portion to rotate with a contact point between the gripping portion and the medical instrument as a center, or causes the imaging portion to rotate so that the contact point is rotationally moved.

With the aforementioned configuration, when the imaging portion is inserted into the body with the medical instrument, by the external force from the medical instrument, the insertion is enabled with the posture of the imaging portion with respect to the medical instrument being maintained. On the other hand, when the imaging portion is retrieved from the inside of the body, the imaging portion is rotated by an external force from a member other than the medical instrument, and thereby inclination of the imaging portion is able to be optimized and this rotation facilitates the retrieval of the imaging portion.

With the aforementioned configuration, since the gripping portion is able to be used both at a time of insertion and at a time of retrieval, it becomes possible to easily retrieve the imaging portion from the inside of the body.

In the in-body monitoring camera system according to an aspect 2 of the invention, in the aspect 1, the at least one gripping portion includes a plurality of grooves, and each of the plurality of grooves extends so as to be a circular arc in top view or a circle in top view and is not formed on an edge of the gripping portion.

In the in-body monitoring camera system according to an aspect 3 of the invention, in the aspect 2, spacing between two of the grooves adjacent to each other in a vicinity of the edge of the at least one gripping portion is less than spacing between two of the grooves adjacent to each other in a center of the gripping portion and spacing between two of the grooves adjacent to each other in a vicinity of the center.

In the in-body monitoring camera system according to an aspect 4 of the invention, in any one of the aspects 1 to 3, an elastic material is formed on the at least one gripping portion.

In the in-body monitoring camera system according to an aspect 5 of the invention, in any one of the aspects 1 to 4, the at least one gripping portion has a shape which gradually becomes thin toward the edge of the gripping portion.

In the in-body monitoring camera system according to an aspect 6 of the invention, in any one of the aspects 1 to 5, the imaging portion includes a housing (camera housing 21), the at least one gripping portion is provided so as to project from the housing, and a length of the gripping portion in a projecting direction of the gripping portion is equal to or more than a radius and equal to or less than a diameter of a circle which constitutes the external shape of the gripping portion.

The invention is not limited to each of the embodiments described above, and may be modified in various manners within the scope of the claims and an embodiment achieved by appropriately combining technical means disclosed in each of different embodiments is also encompassed in the technical scope of the invention. Further, by combining the technical means disclosed in each of the embodiments, a new technical feature may be formed.

INDUSTRIAL APPLICABILITY

The invention is able to be used for an in-body monitoring camera system including an imaging portion which is introduced into a body, and is able to be suitably used particularly for endoscopic surgery and the like.

REFERENCE SIGNS LIST 11 camera unit (imaging portion)
21 camera housing (housing)
22 gripping portion
22c circle
22e edge
33 forceps (medical instrument)
50 to 53 groove
54 elastic material
61 contact point

The invention claimed is:

1. An in-body monitoring camera system, comprising an imaging portion which is introduced into a body, wherein
the imaging portion includes at least one gripping portion which has an external shape that is a circular arc shape in top view,
the at least one gripping portion is at least one sheet member that includes a plurality of grooves, and
each of the plurality of grooves extends so as to be in a circular arc shape in top view or in a circle shape in top view and is not formed on an edge of the gripping portion.

2. The in-body monitoring camera system according to claim 1, wherein
spacing between two of the grooves adjacent to each other in a vicinity of the edge of the at least one gripping portion is less than spacing between two of the grooves adjacent to each other in a center of the gripping portion and spacing between two of the grooves adjacent to each other in a vicinity of the center.

3. The in-body monitoring camera system according to claim 1, wherein
an elastic material is formed on the at least one gripping portion.

4. The in-body monitoring camera system according to claim 1, wherein
the at least one gripping portion has a shape which gradually becomes thin toward the edge of the gripping portion.

5. The in-body monitoring camera system according to claim 1, wherein
the imaging portion includes a housing,
the at least one gripping portion is provided so as to project from the housing, and
a length of the gripping portion in a projecting direction of the gripping portion is equal to or more than a radius and equal to or less than a diameter of a circle which constitutes the external shape of the gripping portion.

6. An in-body monitoring camera system, comprising an imaging portion which is introduced into a body, wherein
the imaging portion includes at least one gripping portion which has an external shape that is a circular arc shape in top view, and
when the gripping portion receives an external force from a medical instrument gripping the gripping portion, the gripping portion causes the imaging portion to be displaced following displacement of the medical instrument while maintaining a posture of the imaging portion with respect to the medical instrument,
when the gripping portion receives an external force other than the external force from the medical instrument gripping the gripping portion, the gripping portion causes the imaging portion to rotate with a position at which the medical instrument grips the gripping portion as a center of rotation, or causes the imaging portion to rotate so that the position is rotationally moved, and
the at least one gripping portion is at least one sheet member that includes a groove and, when the gripping portion receives an external force other than the external force from the medical instrument gripping the gripping portion, the gripping portion causes the imaging portion to rotate while a tip end of the medical instrument moves along the groove.

7. The in-body monitoring camera system according to claim 6, wherein
the at least one gripping portion includes a plurality of grooves each of which is said groove, and
each of the plurality of grooves extends so as to be in a circular arc shape in top view or in a circle shape in top view and is not formed on an edge of the gripping portion.

* * * * *